US010875014B2

(12) United States Patent
Gane et al.

(10) Patent No.: US 10,875,014 B2
(45) Date of Patent: Dec. 29, 2020

(54) SURFACE-MODIFIED CALCIUM CARBONATE AS CARRIER FOR TRANSITION METAL-BASED CATALYSTS

(71) Applicant: Omya International AG, Oftringen (CH)

(72) Inventors: Patrick A. C. Gane, Rothrist (CH); Samuel Rentsch, Spiegel bei Bern (CH); Matthias Welker, Hésingue (FR)

(73) Assignee: Omya International AG, Blue Ash, OH (US)

( * ) Notice: Subject to any disclaimer, the term of this patent is extended or adjusted under 35 U.S.C. 154(b) by 134 days.

(21) Appl. No.: 16/307,819

(22) PCT Filed: Jul. 17, 2017

(86) PCT No.: PCT/EP2017/067974
§ 371 (c)(1),
(2) Date: Dec. 6, 2018

(87) PCT Pub. No.: WO2018/019630
PCT Pub. Date: Feb. 1, 2018

(65) Prior Publication Data
US 2019/0262807 A1 Aug. 29, 2019

Related U.S. Application Data

(60) Provisional application No. 62/369,290, filed on Aug. 1, 2016.

(30) Foreign Application Priority Data

Jul. 25, 2016 (EP) .................................... 16181100

(51) Int. Cl.
*B01J 27/232* (2006.01)
*B01J 21/16* (2006.01)
(Continued)

(52) U.S. Cl.
CPC ............. *B01J 27/232* (2013.01); *B01J 21/16* (2013.01); *B01J 23/42* (2013.01); *B01J 23/44* (2013.01); *B01J 23/72* (2013.01); *B01J 31/1616* (2013.01); *B01J 31/1805* (2013.01); *B01J 31/226* (2013.01); *B01J 31/2226* (2013.01); *B01J 31/2234* (2013.01); *B01J 31/2291* (2013.01); *B01J 31/2295* (2013.01); *B01J 31/2404* (2013.01); *B01J 31/2409* (2013.01); *B01J 35/002* (2013.01); *B01J 35/1014* (2013.01); *B01J 35/1019* (2013.01); *B01J 35/1038* (2013.01); *B01J 35/1042* (2013.01); *B01J 35/1047* (2013.01); *B01J 37/0203* (2013.01); *B01J 37/0209* (2013.01); *B01J 37/28* (2013.01); *C07B 37/04* (2013.01); *C07C 1/321* (2013.01); *C07C 29/00* (2013.01); *C07C 29/60* (2013.01); *C09C 1/021* (2013.01); *C09C 1/022* (2013.01);
(Continued)

(58) Field of Classification Search
CPC . B01J 27/232; B01J 21/16; B01J 23/42; B01J 23/44; B01J 23/72; B01J 31/1616; B01J 31/1805; B01J 31/2226; B01J 31/2234; B01J 31/226; B01J 31/2291; B01J 31/2295; B01J 31/2404; B01J 31/2409; B01J 35/002; B01J 35/1014; B01J 35/1019; B01J 35/1038; B01J 35/1042; B01J 35/1047; B01J 37/0203; B01J 37/0209; B01J 37/28; B01J 37/0036; B01J 37/0201; B01J 37/024; B01J 37/088; B01J 2231/4211; B01J 2231/641; B01J 2523/00; B01J 2531/0205; B01J 2531/16; B01J 2531/824; B01J 2531/828; B01J 2531/842; C07C 1/321; C07C 29/00; C07C 29/60; C07C 31/08; C07C 31/202; C07C 31/205; C07C 2527/232; C07C 2527/236; C07C 2531/02; C07C 1/021; C07C 1/022; C07B 37/04; C01P 2004/61; C01P 2004/80; C01P 2006/12; C01P 2006/14; C01P 2006/16; Y02P 20/52; C09C 1/021; C09C 1/022
USPC ........ 502/152, 156, 162, 174, 328, 331, 339
See application file for complete search history.

(56) References Cited

U.S. PATENT DOCUMENTS 5,625,084 A * 4/1997 Pitchai .................. B01J 23/686
502/347
5,643,415 A * 7/1997 Wise ..................... C01F 11/182
162/181.2
(Continued)

FOREIGN PATENT DOCUMENTS

EP 0924195 * 6/1999 ............. B01J 23/42
EP 0924195 A1 6/1999
(Continued)

OTHER PUBLICATIONS

Nabil Cheikhi et al., "Direct synthesis of methyl isobutyl ketone in gas-phase reaction over palladium-loaded hydroxyapatite." Journal of Catalysis 232, pp. 257-267. (Year: 2005).*
(Continued)

*Primary Examiner* — Patricia L. Hailey
(74) *Attorney, Agent, or Firm* — Schwegman Lundberg & Woessner, P.A.

(57) ABSTRACT

The present invention relates to a catalyst system comprising a transition metal compound on a solid carrier which is a surface-reacted calcium carbonate. The invention further relates to a method for manufacturing said catalyst system and to its use in heterogeneous catalysis.

22 Claims, No Drawings

(51) Int. Cl.
| | |
|---|---|
| B01J 23/42 | (2006.01) |
| B01J 23/44 | (2006.01) |
| B01J 23/72 | (2006.01) |
| B01J 35/10 | (2006.01) |
| B01J 37/02 | (2006.01) |
| B01J 37/28 | (2006.01) |
| C07B 37/04 | (2006.01) |
| C07C 29/60 | (2006.01) |
| B01J 31/22 | (2006.01) |
| C09C 1/02 | (2006.01) |
| B01J 31/24 | (2006.01) |
| B01J 35/00 | (2006.01) |
| B01J 31/16 | (2006.01) |
| B01J 31/18 | (2006.01) |
| C07C 29/00 | (2006.01) |
| C07C 1/32 | (2006.01) |
| C07C 31/08 | (2006.01) |
| C07C 31/20 | (2006.01) |
| B01J 37/08 | (2006.01) |
| B01J 37/00 | (2006.01) |

(52) U.S. Cl.
CPC ........ *B01J 37/0036* (2013.01); *B01J 37/0201* (2013.01); *B01J 37/024* (2013.01); *B01J 37/088* (2013.01); *B01J 2231/4211* (2013.01); *B01J 2231/641* (2013.01); *B01J 2523/00* (2013.01); *B01J 2531/0205* (2013.01); *B01J 2531/16* (2013.01); *B01J 2531/824* (2013.01); *B01J 2531/828* (2013.01); *B01J 2531/842* (2013.01); *C01P 2004/61* (2013.01); *C01P 2004/80* (2013.01); *C01P 2006/12* (2013.01); *C01P 2006/14* (2013.01); *C01P 2006/16* (2013.01); *C07C 31/08* (2013.01); *C07C 31/202* (2013.01); *C07C 31/205* (2013.01); *C07C 2527/232* (2013.01); *C07C 2527/236* (2013.01); *C07C 2531/02* (2013.01); *Y02P 20/52* (2015.11)

(56) References Cited

U.S. PATENT DOCUMENTS

| | | |
|---|---|---|
| 5,703,254 A | 12/1997 | Gaffney et al. |
| 5,965,480 A | 10/1999 | Cooker et al. |
| 2004/0020410 A1 | 2/2004 | Gane et al. |
| 2005/0027134 A1* | 2/2005 | Hooks .................. B01J 23/50 549/536 |
| 2017/0157171 A1* | 6/2017 | Gerard .................. A61K 8/19 |
| 2020/0042149 A1* | 2/2020 | Hatambeiki .......... G06F 3/0484 |

FOREIGN PATENT DOCUMENTS

| | | | |
|---|---|---|---|
| EP | 2 264 108 A1 | 12/2010 | |
| EP | 2 264 109 A1 | 12/2010 | |
| EP | 2 371 766 A1 | 10/2011 | |
| EP | 2 447 213 A1 | 5/2012 | |
| EP | 2 524 898 A1 | 11/2012 | |
| EP | 2719373 A1 * | 4/2014 | ............... A61K 9/00 |
| EP | 2719376 A1 * | 4/2014 | ............... A61K 9/16 |
| EP | 2 840 065 A1 | 2/2015 | |
| EP | 3 034 070 A1 | 6/2016 | |
| EP | 3 045 042 A1 | 7/2016 | |
| EP | 3149088 A1 | 4/2017 | |
| EP | 3 176 222 A1 | 6/2017 | |
| RU | 2213728 C2 | 10/2003 | |
| WO | 96/01242 A1 | 1/1996 | |
| WO | 00/39222 A1 | 7/2000 | |
| WO | 2004/030813 A1 | 4/2004 | |
| WO | 2004/083316 A1 | 9/2004 | |
| WO | 2005/121257 A2 | 12/2005 | |
| WO | 2009/074492 A1 | 6/2009 | |
| WO | 2013/142473 A1 | 9/2013 | |
| WO | 2013/190076 A1 | 12/2013 | |

OTHER PUBLICATIONS

Najwa Takarrounnt et al., "Characaterization and performance of the bifunctional platinum-loaded calcium-hydroxyapatite in the one-step synthesis of methyl isobutyl ketone." Journal of Molecular Catalysis A: Chemical 377, pp. 42-50. (Year: 2013).*

Jeroen ten Dam et al., "Tuning selectivity of Pt/CaCO3 in glycerol hydrogenolysis—A Design of Experiments approach." Catalysis Communications 13, pp. 1-5. (Year: 2011).*

Minfeng Zeng et al., "An efficient and recyclable heterogeneous palladium catalyst utilizing naturally abundant pearl shell waste." Green Chemistry 13, pp. 350-356. (Year: 2011).*

The International Search Report dated Oct. 18, 2017 from PCT/EP2017/067974.

The Written Opinion of the International Searching Authority dated Oct. 18, 2017 from PCT/EP2017/067974.

Dam et al., "Tuning Selectivity of Pt/CaCO3 in Glycerol Hydrogenolysis—A Design of Experiments Approach," Catalysis Communications, vol. 13, No. 1, Jun. 6, 2011, pp. 1-5.

Zeng et al., "An Efficient and Recyclable Heterogeneous Palladium Catalyst Utilizing Naturally Abundant Pearl Shell Waste," Green Chemistry, vol. 13, No. 2, Dec. 24, 2010, pp. 350-356.

* cited by examiner

SURFACE-MODIFIED CALCIUM CARBONATE AS CARRIER FOR TRANSITION METAL-BASED CATALYSTS

CROSS-REFERENCE TO RELATED APPLICATIONS

This is a U.S. national phase of PCT Application No. PCT/EP2017/067974, filed Jul. 17, 2017, which claims priority to U.S. Provisional Application No. 62/369,290, filed Aug. 1, 2016, and European Application No. 16181100.5, filed Jul. 25, 2016.

The present invention relates to a catalyst system comprising a transition metal compound on a solid carrier which is a surface-reacted calcium carbonate and to a method for manufacturing said catalyst system. The invention further relates to the use of said catalyst system in granules or mouldings. The catalyst system and corresponding granules or mouldings may be used in various transition metal-catalysed reactions.

Combined carrier/catalyst systems are widely used in heterogeneous catalysis and have several advantages. For example, the handling of such catalyst systems and also the isolation of reaction products is less expensive compared with conventional homogenous systems. Furthermore, the activity and efficiency of a catalyst system in a given reaction may be controlled by selecting specific structural properties of the carrier.

Elemental transition metals and corresponding compounds, such as transition metal salts or complexes, are well-known catalysts and may be applied in a number of reactions, for example in alkene or alkyne hydrogenation or in epoxidation. The most frequently used transition metals include platinum, palladium and copper.

Common support materials for heterogeneous transition metal catalysis are activated carbon, carbon black/graphite, alumina, barium sulphate and calcium carbonate (The Catalyst Technical Handbook, Johnson Matthey Co., 2005).

For example, U.S. Pat. No. 5,965,480 and U.S. Pat. No. 5,703,254 disclose the direct oxidation of propylene to propylene oxide using silver catalysts on alkaline earth metal carbonate-containing carriers, such as calcium carbonate, to catalyze selectively the formation of epoxides.

WO 2004/030813 A1 relates to a process for preparing a catalyst which involves (a) preparing a paste having a uniform mixture of at least one alkaline earth metal carbonate, a liquid medium, a silver bonding additive, and at least one extrusion aid and/or optionally a burnout additive; (b) forming one or more shaped particles from the paste; (c) drying and calcining the particles; and (e) impregnating the dried and calcined particles with a solution containing a silver compound. Said alkaline earth metal carbonate may be calcium carbonate.

WO 96/01242 A1 discloses a process for the selective hydrogenation of 1,4-butynediol to 1,4-butenediol using a palladium catalyst to which copper and zinc or silver and zinc are added as doping agents. The catalyst may be provided on a solid support. The support material may be calcium carbonate, for example precipitated calcium carbonate.

WO 2013/190076 A1 relates to a catalytic system, which is a Lindlar type catalyst, wherein the support material (calcium carbonate) has an average particle size ($d_{50}$) of more than 10 μm. It further discloses the use of such a catalytic system for the partial hydrogenation of a carbon-carbon triple bond to a double bond. Specific examples of carrier materials include precipitated calcium carbonate.

However, the toxicity of transition metals and corresponding salts is a general drawback and therefore the catalyst loadings in transition metal-catalysed reactions should be kept as low as possible. A further drawback of transition metals may be seen in the rare availability of natural resources and in high costs for procurement and recycling, if possible at all. Accordingly, there is a continuous need for the improvement of catalyst systems to overcome one or more of the aforementioned drawbacks.

One object of the present invention may therefore be seen in the provision of a more efficient catalyst system which allows to reduce the catalyst loading during catalysis and the overall consumption of transition metals.

A further object of the present invention may be seen in the provision of a time-saving catalyst system with higher turnover rates.

Yet one further object may be seen in the provision of an easily recyclable catalyst system to reduce the overall consumption of transition metals.

One further object may therefore be seen in the provision of a more environmentally compatible catalyst system.

Finally, one further object of the present invention may be seen in the provision of more cost-effective catalytic reaction systems.

The foregoing and other problems may be solved by the subject-matter as defined herein in the independent claims.

In this respect, a first aspect of the present invention relates to a catalyst system comprising a transition metal compound on a solid carrier, wherein the solid carrier is a surface-reacted calcium carbonate comprising ground natural calcium carbonate (GNCC) or precipitated calcium carbonate (PCC), and at least one water-insoluble calcium salt other than calcium carbonate, and wherein the surface-reacted calcium carbonate shows:

(i) a specific surface area of from 15 to 200 $m^2/g$ measured using nitrogen and the BET method according to ISO 9277:2010;
(ii) an intra-particle intruded specific pore volume in the range of from 0.1 to 2.3 $cm^3/g$ calculated from mercury porosimetry measurement; and
(iii) a ratio of the at least one water-insoluble calcium salt to calcite, aragonite and/or vaterite in the range of from 1:99 to 99:1.

The inventors of the present application surprisingly found that the use of surface-reacted calcium carbonate (SRCC) as catalyst carrier in transition metal catalysis provides several advantages. Surface-reacted calcium carbonate is a reaction product of ground natural calcium carbonate (GNCC) or precipitated calcium carbonate (PCC) treated with $CO_2$ and one or more $H_3O^+$ ion donors, wherein the $CO_2$ is formed in situ by the $H_3O^+$ ion donors treatment. Additionally or alternatively, $CO_2$ may be supplied from an external source. Because of the reaction of GNCC or PCC with $CO_2$ and one or more $H_3O^+$ ion donors, SRCC comprises ground natural calcium carbonate (GNCC) or precipitated calcium carbonate (PCC), and at least one water-insoluble calcium salt other than calcium carbonate resulting from the foregoing reaction. Said material has specific surface properties and was found to be surprisingly useful as carrier material in heterogeneous catalysis.

For example, higher conversion rates in C-C cross coupling reactions and higher catalytic activities in glycerol hydrogenolysis were achieved with the catalyst systems according to the present invention. Moreover, the inventive catalyst system was easier to recover and higher yields were achieved, for example, in a second catalytic cycle compared with conventional carrier systems.

Another aspect of the present invention relates to a method for manufacturing a catalyst system comprising a transition metal compound on a solid carrier, the method comprising the following steps:

(a) providing at least one surface-reacted calcium carbonate comprising ground natural calcium carbonate (GNCC) or precipitated calcium carbonate (PCC), and at least one water-insoluble calcium salt other than calcium carbonate;
(b) providing at least one transition metal compound; and
(c) contacting in a liquid medium, the surface-reacted calcium carbonate provided in step (a) and the transition metal compound provided in step (b) to obtain a mixture comprising surface-reacted calcium carbonate and a transition metal compound;

wherein the surface-reacted calcium carbonate shows:

(i) a specific surface area of from 15 to 200 m$^2$/g measured using nitrogen and the BET method according to ISO 9277:2010;
(ii) an intra-particle intruded specific pore volume in the range of from 0.1 to 2.3 cm$^3$/g calculated from mercury porosimetry measurement; and
(iii) a ratio of the at least one water-insoluble calcium salt to calcite, aragonite and/or vaterite in the range of from 1:99 to 99:1.

Still another aspect of the present invention relates to the inventive catalyst system which is obtainable according to the foregoing method.

Still another aspect of the present invention relates to the use of said catalyst system in a process comprising the following steps:

(a) providing one or more reactants;
(b) providing the inventive catalyst system;
(c) subjecting the one or more reactants provided in step (a) to a chemical reaction in the presence of the catalyst system provided in step (b).

Still another aspect of the present invention relates to the use of surface-reacted calcium carbonate as described herein as carrier for transition metal-based catalysts.

Finally, another aspect of the present invention relates to granules, mouldings or extrudates comprising the inventive catalyst system.

It should be understood that for the purposes of the present invention, the following terms will have the following meanings:

"Ground natural calcium carbonate" (GNCC) in the meaning of the present invention is a calcium carbonate obtained from natural sources, such as limestone, marble, or chalk, and processed through a wet and/or dry treatment such as grinding, screening and/or fractionation, for example, by a cyclone or classifier.

"Precipitated calcium carbonate" (PCC) in the meaning of the present invention is a synthesised material, generally obtained by precipitation following a reaction of carbon dioxide and calcium hydroxide (hydrated lime) in an aqueous environment or by precipitation of a calcium- and a carbonate source in water. Additionally, precipitated calcium carbonate can also be the product of introducing calcium- and carbonate salts, calcium chloride and sodium carbonate for example, in an aqueous environment. PCC may have a vateritic, calcitic or aragonitic crystalline form. PCCs are described, for example, in EP 2 447 213 A1, EP 2 524 898 A1, EP 2 371 766 A1, EP 2 840 065 A1, or WO 2013/142473 A1.

A "surface-reacted calcium carbonate" according to the present invention is a reaction product of ground natural calcium carbonate (GNCC) or precipitated calcium carbonate (PCC) treated with $CO_2$ and one or more $H_3O^+$ ion donors, wherein the $CO_2$ is formed in situ by the $H_3O^+$ ion donors treatment and/or is supplied from an external source. A $H_3O^+$ ion donor in the context of the present invention is a Bronsted acid and/or an acid salt.

The "particle size" of surface-reacted calcium carbonate herein is described as volume-based particle size distribution $d_x(vol)$. Therein, the value $d_x(vol)$ represents the diameter relative to which x % by volume of the particles have diameters less than $d_x(vol)$. This means that, for example, the $d_{20}(vol)$ value is the particle size at which 20 vol.-% of all particles are smaller than that particle size. The $d_{50}(vol)$ value is thus the volume median particle size, i.e. 50 vol.-% of all particles are smaller than that particle size and the $d_{98}(vol)$ value is the particle size at which 98 vol.-% of all particles are smaller than that particle size.

The "particle size" of particulate materials other than surface-reacted calcium carbonate herein is described by its distribution of particle sizes $d_x(wt)$. Therein, the value $d_x(wt)$ represents the diameter relative to which x % by weight of the particles have diameters less than $d_x(wt)$. This means that, for example, the $d_{20}(wt)$ value is the particle size at which 20 wt.-% of all particles are smaller than that particle size. The $d_{50}(wt)$ value is thus the weight median particle size, i.e. 50 wt.-% of all particles are smaller than that particle size.

Throughout the present document, the "specific surface area" (in m$^2$/g) of surface-reacted calcium carbonate or other materials is determined using the BET method (using nitrogen as adsorbing gas), which is well known to the skilled man (ISO 9277:2010).

For the purpose of the present invention the "porosity" or "pore volume" refers to the intra-particle intruded specific pore volume. Said porosity or pore volume is measured using a Micromeritics Autopore V 9620 mercury porosimeter.

"Water-insoluble" materials are defined as materials which, when 100 g of said material is mixed with 100 g deionised water and filtered on a filter having a 0.2 µm pore size at 20° C. to recover the liquid filtrate, provide less than or equal to 1 g of recovered solid material following evaporation at 95 to 100° C. of 100 g of said liquid filtrate at ambient pressure. "Water-soluble" materials are thus defined as materials which, when 100 g of said material is mixed with 100 g deionised water and filtered on a filter having a 0.2 µm pore size at 20° C. to recover the liquid filtrate, provide more than 1 g of recovered solid material following evaporation at 95 to 100° C. of 100 g of said liquid filtrate at ambient pressure.

A "suspension" or "slurry" in the meaning of the present invention comprises insoluble solids and a liquid medium, for example water, and optionally further additives, and usually contains large amounts of solids and, thus, is more viscous and can be of higher density than the liquid from which it is formed.

The term "solid" according to the present invention refers to a material that is solid under standard ambient temperature and pressure (SATP) which refers to a temperature of 298.15 K (25° C.) and an absolute pressure of exactly 1 bar. The solid may be in the form of a powder, tablet, granules, flakes etc. Accordingly, the term "liquid medium" refers to a material that is liquid under standard ambient temperature and pressure (SATP) which refers to a temperature of 298.15 K (25° C.) and an absolute pressure of exactly 1 bar.

Where the term "comprising" is used in the present description and claims, it does not exclude other non-specified elements of major or minor functional importance.

For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Whenever the terms "including" or "having" are used, these terms are meant to be equivalent to "comprising" as defined above.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This, e.g., means that, unless the context clearly dictates otherwise, the term "obtained" does not mean to indicate that, e.g., an embodiment must be obtained by, e.g. the sequence of steps following the term "obtained" even though such a limited understanding is always included by the terms "obtained" or "defined" as a preferred embodiment.

Advantageous embodiments of the inventive catalyst system, the corresponding method of manufacturing said catalyst system and uses of said catalyst system are defined hereinafter as well as in the corresponding subclaims.

In one embodiment according to the present invention, the at least one water-insoluble calcium salt is selected from the group consisting of octacalcium phosphate, hydroxylapatite, chlorapatite, fluorapatite, carbonate apatite and mixtures thereof, preferably the at least one water-insoluble calcium salt is hydroxylapatite.

In a further embodiment, the ratio of the at least one water-insoluble calcium salt to calcite, aragonite and/or vaterite, preferably to calcite, is in the range of from 1:9 to 9:1, preferably from 1:7 to 8:1, more preferably from 1:5 to 7:1 and even more preferably from 1:4 to 7:1 by weight.

According to another embodiment, the transition metal compound is selected from the group consisting of palladium compounds, platinum compounds, copper compounds and mixtures thereof.

According to still another embodiment of the inventive catalyst system, the transition metal compound is selected from the group consisting of elemental palladium, $Pd(acac)_2$, $Na_2PdCl_4$, $Pd(OAc)_2$, $Pd(PPh_3)_4$, $PdCl_2(PPh_3)_2$, $(dppf)PdCl_2$, $(dppe)PdCl_2$, $(dppp)PdCl_2$, $(dppb)PdCl_2$, $PdCl_2$, $(C_3H_5PdCl)_2$, bis(acetate)triphenylphosphine-palladium(II), $Pd(dba)_2$, $Pd(H_2NCH_2CH_2NH_2)Cl_2$, elemental platinum, $Na_2PtCl_6$ $Pt(acac)_2$, $Na_2PtCl_4$, $H_2PtCl_6$, $(NH_4)_2[PtCl_6]$, $PtO_2.H_2O$, $PtCl_4$, elemental copper, $Cu_2O$, $Cu_2S$, copper(I)-thiophene-2-carboxylate, CuBr, CuCN, CuCl, CuF, CuI, CuH, CuSCN, $CuBr_2$, $CuCO_3$, $CuCl_2$, $CuF_2$, $Cu(NO_3)_2$, $Cu_3(PO_4)_2$, CuO, $CuO_2$, $Cu(OH)_2$, $CuI_2$, CuS, $CuSO_4$, $Cu_2(OAc)_4$ and mixtures thereof, preferably the transition metal compound is selected from the group consisting of elemental palladium, $Pd(acac)_2$, $Na_2PdCl_4$, $Pd(OAc)_2$, $Pd(PPh_3)_4$, $PdCl_2(PPh_3)_2$, $(dppf)PdCl_2$, $(dppe)PdCl_2$, $(dppp)PdCl_2$, $(dppb)PdCl_2$, $PdCl_2$, $(C_3H_5PdCl)_2$, bis(acetate)triphenyl-phosphine-palladium(II), $Pd(dba)_2$, $Pd(H_2NCH_2CH_2NH_2)Cl_2$, elemental platinum, $Na_2PtCl_6$ $Pt(acac)_2$, $Na_2PtCl_4$, $H_2PtCl_6$, $(NH_4)_2[PtCl_6]$, $PtO_2.H_2O$, $PtCl_4$ and mixtures thereof.

According to still another embodiment, the surface-reacted calcium carbonate has:
 (i) a specific surface area in the range of from 27 to 180 $m^2/g$, preferably from 25 to 160 $m^2/g$ and more preferably from 30 to 150 $m^2/g$, measured using nitrogen and the BET method according to ISO 9277:2010;
 (ii) a $d_{50}(vol)$ in the range of from 1 to 75 μm, preferably from 2 to 50 μm, more preferably from 3 to 40 μm, even more preferably from 4 to 30 μm and most preferably from 5 to 15 μm;
 (iii) a $d_{98}(vol)$ in the range of from 2 to 150 μm, preferably from 4 to 100 μm, more preferably from 6 to 80 μm, even more preferably from 8 to 60 μm and most preferably from 10 to 30 μm; and/or
 (iv) an intra-particle intruded specific pore volume in the range of from 0.2 to 2.0 $cm^3/g$, preferably from 0.4 to 1.8 $cm^3/g$ and most preferably from 0.6 to 1.6 $cm^3/g$, calculated from mercury porosimetry measurement.

In still another embodiment, the inventive catalyst further comprises one or more reaction products obtained by reaction of the transition metal compound and the surface-reacted calcium carbonate.

According to still another embodiment, the content of the transition metal compound and/or the one or more reaction products thereof is in the range of from 0.1 to 60 wt.-%, preferably from 0.1 to 30 wt.-%, more preferably 0.1 to 20 wt.-%, even more preferably from 0.1 to 10 wt.-% and most preferably from 0.2 to 5 wt.-%, based on the weight of the transition metal compound per total weight of the catalyst system.

In one embodiment of the method according to the present invention, said method is characterised in that:
 (i) the at least one surface-reacted calcium carbonate of step (a) is provided in a liquid medium in form of a suspension; and/or
 (ii) the at least one transition metal compound of step (b) is provided in a liquid medium in form of a solution or a suspension, preferably in form of a solution.

In a further embodiment, the method comprising steps (a) to (c) further comprises step (d) of removing at least part of the liquid medium contained in the mixture of step (c) by evaporation and/or filtration to obtain a concentrated mixture.

According to another embodiment, the inventive method further comprises step (e) of thermally treating the mixture of step (c) or the concentrated mixture of step (d) at a temperature of below 400° C., preferably at a temperature in the range from 170° C. to 400° C., more preferably from 200° C. to 300° C., even more preferably from 250° C. to 310° C. and most preferably from 280° C. to 320° C.

According to still another embodiment of the inventive method, the transition metal compound is selected from the group consisting of palladium compounds, platinum compounds, copper compounds and mixtures thereof.

In still another embodiment of the method according to the present invention, the transition metal compound is selected from the group consisting of elemental palladium, $Pd(acac)_2$, $Na_2PdCl_4$, $Pd(OAc)_2$, $Pd(PPh_3)_4$, $PdCl_2(PPh_3)_2$, $(dppf)PdCl_2$, $(dppe)PdCl_2$, $(dppp)PdCl_2$, $(dppb)PdCl_2$, $PdCl_2$, $(C_3H_5PdCl)_2$, bis(acetate)triphenyl-phosphine-palladium(II), $Pd(dba)_2$, $Pd(H_2NCH_2CH_2NH_2)Cl_2$, elemental platinum, $Na_2PtCl_6$ $Pt(acac)_2$, $Na_2PtCl_4$, $H_2PtCl_6$, $(NH_4)_2[PtCl_6]$, $PtO_2.H_2O$, $PtCl_4$, elemental copper, $Cu_2O$, $Cu_2S$, copper(I)-thiophene-2-carboxylate, CuBr, CuCN, CuCl, CuF, CuI, CuH, CuSCN, $CuBr_2$, $CuCO_3$, $CuCl_2$, $CuF_2$, $Cu(NO_3)_2$, $Cu_3(PO_4)_2$, CuO, $CuO_2$, $Cu(OH)_2$, $CuI_2$, CuS, $CuSO_4$, $Cu_2(OAc)_4$ and mixtures thereof, preferably the transition metal compound is selected from the group consisting of elemental palladium, $Pd(acac)_2$, $Na_2PdCl_4$, $Pd(OAc)_2$, $Pd(PPh_3)_4$, $PdCl_2(PPh_3)_2$, $(dppf)PdCl_2$, $(dppe)PdCl_2$, $(dppp)PdCl_2$, $(dppb)PdCl_2$, $PdCl_2$, $(C_3H_5PdCl)_2$, bis(acetate)triphenyl-phosphine-palladium(II), $Pd(dba)_2$, Pd(H$_2$NCH$_2$CH$_2$NH$_2$)Cl$_2$, elemental platinum, Na$_2$PtCl$_6$ Pt(acac)$_2$, Na$_2$PtCl$_4$, H$_2$PtCl$_6$, (NH$_4$)$_2$[PtCl$_6$], PtO$_2$.H$_2$O, PtCl$_4$ and mixtures thereof.

In another embodiment of the inventive process, the liquid medium is a non-polar solvent, a polar solvent or a mixture thereof, preferably the non-polar solvent is selected from the group consisting of pentane, cyclopentane, hexane, cyclohexane, benzene, toluene, 1,4-dioxane, chloroform, diethyl ether, dichloromethane and mixtures thereof and/or the polar solvent is selected from the group consisting of tetrahydrofuran, ethyl acetate, acetone, dimethylformamide, acetonitrile, dimethyl sulphoxide, nitromethane, propylene carbonate, formic acid, n-butanol, isopropanol, n-propanol, ethanol, methanol, acetic acid, water and mixtures thereof.

In still another embodiment, the transition metal compound is Na$_2$PdCl$_4$ and/or Na$_2$PtCl$_4$ and the liquid medium is a polar solvent, preferably water; and/or the transition metal compound is Pd(acac)$_2$ and/or Pt(acac)$_2$ and the liquid medium is a non-polar solvent, preferably toluene.

According to another embodiment, the inventive catalyst system is used in a catalytic process comprising steps (a) to (c), wherein said process further comprises step (d) of recovering and recycling the catalyst system.

According to another embodiment, the inventive catalyst system is used in a catalytic process comprising a chemical reaction selected from one or more of the following reaction types: hydrogenolyses, C—C couplings and C—C cross couplings, C—N cross couplings, C—O cross couplings, C—S cross couplings, cycloaddition reactions, alkene hydrogenations and alkyne hydrogenations, allylic substitutions, reductions of nitro groups and hydrocarbonylations of aryl halides, preferably hydrogenolyses, C—C couplings and C—C cross couplings.

As set out hereinabove, the process for the provision of the inventive catalyst system comprises steps (a)-(c). Said process optionally further comprises steps (d) and (e). It should be understood, that the process of the present invention may be carried out as a continuous process or as a batch process. Preferably, the inventive process is carried out as a continuous process.

In the following, it is referred to further details of the present invention and especially to the foregoing steps of the inventive process for the surface-treatment of a surface-reacted calcium carbonate.

Step (a): Providing at Least One Surface-Reacted Calcium Carbonate

According to step (a) of the process of the present invention, a surface-reacted calcium carbonate is provided. Surface-reacted calcium carbonate is also referred to as functionalised calcium carbonate (FCC).

It is appreciated that the surface-reacted calcium carbonate can be one or more surface-reacted calcium carbonate(s).

In one embodiment of the present invention, the surface-reacted calcium carbonate comprises, preferably consists of, one kind of surface-reacted calcium carbonate. Alternatively, the surface-reacted calcium carbonate comprises, preferably consists of, two or more kinds of surface-reacted calcium carbonates. For example, the surface-reacted calcium carbonate comprises, preferably consists of, two or three kinds of surface-reacted calcium carbonates.

Preferably, the surface-reacted calcium carbonate comprises, more preferably consists of, one kind of surface-reacted calcium carbonate.

The surface-reacted calcium carbonate is a reaction product of ground natural calcium carbonate (GNCC) or precipitated calcium carbonate (PCC) treated with CO$_2$ and one or more H$_3$O$^+$ ion donors, wherein the CO$_2$ is formed in situ by the H$_3$O$^+$ ion donors treatment and/or is supplied from an external source. Because of the reaction of ground natural calcium carbonate or precipitated calcium carbonate with CO$_2$ and the one or more H$_3$O$^+$ ion donors, surface-reacted calcium carbonate comprises GNCC or PCC and at least one water-insoluble calcium salt.

In a preferred embodiment, said surface-reacted calcium carbonate comprises GNCC or PCC and at least one water-insoluble calcium salt which is present on at least part of the surface of said GNCC or PCC.

An H$_3$O$^+$ ion donor in the context of the present invention is a Brnsted acid and/or an acid salt.

In a preferred embodiment of the invention, the surface-reacted calcium carbonate is obtained by a process comprising the steps of:
(a) providing a suspension of ground natural calcium carbonate (GNCC) or precipitated calcium carbonate (PCC);
(b) adding at least one acid having a pK$_a$ value of 0 or less at 20° C., or having a pK$_a$ value from 0 to 2.5 at 20° C. to the suspension provided in step (a); and
(c) treating the suspension provided in step (a) with CO$_2$ before, during or after step (b).

According to another embodiment, the surface-reacted calcium carbonate is obtained by a process comprising the steps of:
(a) providing a ground natural calcium carbonate (GNCC) or precipitated calcium carbonate (PCC);
(b) providing at least one water-soluble acid;
(c) providing gaseous CO$_2$; and
(d) contacting said GNCC or PCC provided in step (a), the at least one acid provided in step (b) and the gaseous CO$_2$ provided in step (c);
characterised in that (i) the at least one acid provided in step (b) has a pK$_a$ of greater than 2.5 and less than or equal to 7 at 20° C., associated with the ionisation of its first available hydrogen, and a corresponding anion is formed on loss of this first available hydrogen capable of forming a water-soluble calcium salt; and (ii) following contacting the at least one water-soluble acid provided in step (b) and the GNCC or PCC provided in step (a), at least one water-soluble salt, which in the case of a hydrogen-containing salt has a pK$_a$ of greater than 7 at 20° C., associated with the ionisation of the first available hydrogen, and the salt anion of which is capable of forming water-insoluble calcium salts, is additionally provided.

The source of calcium carbonate, e.g. "ground natural calcium carbonate" (GNCC), preferably is selected from calcium carbonate-containing minerals selected from the group comprising marble, chalk, limestone and mixtures thereof. Natural calcium carbonate may comprise further naturally occurring components such as magnesium carbonate, alumino silicate etc. According to one embodiment, natural calcium carbonate, such as GNCC, comprises aragonitic, vateritic or calcitic mineralogical crystal forms of calcium carbonate or mixtures thereof.

In general, the grinding of ground natural calcium carbonate may be performed in a dry or wet grinding process and may be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled person. In case the ground natural calcium carbonate comprises wet ground calcium carbonate, the grinding step may be performed under conditions such that autogenous grinding takes place and/or by horizontal ball milling, and/or other such processes known to the skilled person. The wet processed ground natural calcium carbonate thus obtained may be washed and dewatered by well-known processes, e.g. by flocculation, filtration or forced evaporation prior to drying. The subsequent step of drying (if necessary) may be carried out in a single step such as spray drying, or in at least two steps. It is also common that such a mineral material undergoes a beneficiation step (such as a flotation, bleaching or magnetic separation step) to remove impurities.

A "precipitated calcium carbonate" (PCC) in the meaning of the present invention is a synthesised material, generally obtained by precipitation following a reaction of $CO_2$ and calcium hydroxide in an aqueous environment or by precipitation of calcium and carbonate ions, for example $CaCl_2$ and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S—PCC), rhombohedral (R—PCC), hexagonal prismatic, pinacoidal, colloidal (C—PCC), cubic, and prismatic (P—PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained aqueous PCC slurry can be mechanically dewatered and dried.

According to one embodiment of the present invention, the precipitated calcium carbonate comprises aragonitic, vateritic or calcitic mineralogical crystal forms of calcium carbonate or mixtures thereof.

Precipitated calcium carbonate may be ground prior to the treatment with $CO_2$ and at least one $H_3O^+$ ion donor by the same means as used for grinding natural calcium carbonate and described above.

According to one embodiment of the present invention, the natural or precipitated calcium carbonate is in form of particles having a weight median particle size $d_{50}(wt)$ of from 0.05 to 10.0 µm, preferably from 0.2 to 5.0 µm, more preferably from 0.4 to 3.0 µm, most preferably from 0.6 to 1.2 µm, and especially 0.7 µm. According to a further embodiment of the present invention, the natural or precipitated calcium carbonate is in form of particles having a top cut particle size $d_{98}(wt)$ of from 0.15 to 55 µm, preferably from 1 to 40 µm, more preferably from 2 to 25 µm, most preferably from 3 to 15 µm, and especially 4µm.

The natural or precipitated calcium carbonate may be used dry or suspended in water. Preferably, a corresponding aqueous slurry has a content of natural or precipitated calcium carbonate within the range of from 1 to 90 wt.-%, more preferably from 3 to 60 wt.-%, even more preferably from 5 to 40 wt.-%, and most preferably from 10 to 25 wt.-%, based on the total weight of said slurry.

The one or more $H_3O^+$ ion donor used for the preparation of surface reacted calcium carbonate may be any strong acid, medium-strong acid, or weak acid, or mixtures thereof, generating $H_3O^+$ ions under the preparation conditions. According to the present invention, the at least one $H_3O^+$ ion donor can also be an acid salt, generating $H_3O^+$ ions under the preparation conditions.

According to one embodiment, the at least one $H_3O^+$ ion donor is a strong acid having a $pK_a$ of 0 or less at 20° C.

According to another embodiment, the at least one $H_3O^+$ ion donor is a medium-strong acid having a $pK_a$ value from 0 to 2.5 at 20° C. If the $pK_a$ at 20° C. is 0 or less, the acid is preferably selected from sulphuric acid, hydrochloric acid, or mixtures thereof. If the $pK_a$ at 20° C. is from 0 to 2.5, the $H_3O^+$ ion donor is preferably selected from $H_2SO_3$, $H_3PO_4$, oxalic acid, or mixtures thereof. The at least one $H_3O^+$ ion donor can also be an acid salt, for example, $HSO_4^-$ or $H_2PO_4^-$, being at least partially neutralised by a corresponding cation such as $Li^+$, $Na^+$ or $K^+$, or $HPO_4^{2-}$, being at least partially neutralised by a corresponding cation such as $Li^+$, $Na^+$, $K^+$, $Mg^{2+}$ or $Ca^{2+}$. The at least one $H_3O^+$ ion donor can also be a mixture of one or more acids and one or more acid salts.

According to still another embodiment, the at least one $H_3O^+$ ion donor is a weak acid having a $pK_a$ value of greater than 2.5 and less than or equal to 7, when measured at 20° C., associated with the ionisation of the first available hydrogen, and having a corresponding anion, which is capable of forming water-soluble calcium salts. Subsequently, at least one water-soluble salt, which in the case of a hydrogen-containing salt has a $pK_a$ of greater than 7, when measured at 20° C., associated with the ionisation of the first available hydrogen, and the salt anion of which is capable of forming water-insoluble calcium salts, is additionally provided. According to a more preferred embodiment, the weak acid has a $pK_a$ value from greater than 2.5 to 5 at 20° C., and more preferably the weak acid is selected from the group consisting of acetic acid, formic acid, propanoic acid and mixtures thereof. Exemplary cations of said water-soluble salt are selected from the group consisting of potassium, sodium, lithium and mixtures thereof. In a more preferred embodiment, said cation is sodium or potassium. Exemplary anions of said water-soluble salt are selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water-soluble salt addition may be performed dropwise or in one step. In the case of drop wise addition, this addition preferably takes place within a time period of 10 min. It is more preferred to add said salt in one step.

According to one embodiment of the present invention, the at least one $H_3O^+$ ion donor is selected from the group consisting of hydrochloric acid, sulphuric acid, sulphurous acid, phosphoric acid, citric acid, oxalic acid, acetic acid, formic acid and mixtures thereof. Preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a corresponding cation such as $Li^+$, $Na^+$ or $K^+$, $HPO_4^2$, being at least partially neutralised by a corresponding cation such as $Li^+$, $Na^+$, $K^+$, $Mg^{2+}$ or $Ca^{2+}$ and mixtures thereof, more preferably the at least one acid is selected from the group consisting of hydrochloric acid, sulphuric acid, sulphurous acid, phosphoric acid, oxalic acid, or mixtures thereof. A particularly preferred $H_3O^+$ ion donor is phosphoric acid.

The one or more $H_3O^+$ ion donor can be added to the suspension as a concentrated solution or a more diluted solution. Preferably, the molar ratio of the $H_3O^+$ ion donor to the natural or precipitated calcium carbonate is from 0.01 to 4, more preferably from 0.02 to 2, even more preferably from 0.05 to 1 and most preferably from 0.1 to 0.58.

In another preferred embodiment, the at least one $H_3O^+$ ion donor is selected from the group consisting of hydrochloric acid, sulphuric acid, sulphurous acid, phosphoric acid, citric acid, oxalic acid, acetic acid, formic acid and mixtures thereof, wherein the molar ratio of the $H_3O^+$ ion donor to the natural or precipitated calcium carbonate is from 0.01 to 4, more preferably from 0.02 to 2, even more preferably from 0.05 to 1 and most preferably from 0.1 to 0.58.

In a particularly preferred embodiment, the at least one $H_3O^+$ ion donor is a mixture of phosphoric acid and citric acid, more preferably the molar ratio of the $H_3O^+$ ion donor to the natural or precipitated calcium carbonate is from 0.01 to 4, more preferably from 0.02 to 2, even more preferably from 0.05 to 1 and most preferably from 0.1 to 0.58.

As already indicated hereinabove, the treatment of GNCC or PCC with the at least one $H_3O^+$ ion donor and $CO_2$ may lead to the formation of at least one water-insoluble calcium salt. Therefore, surface-reacted calcium carbonate comprises GNCC or PCC and at least one water-insoluble calcium salt other than calcium carbonate. In one embodiment, said at least one water-insoluble calcium salt is present on at least part of the surface of said GNCC or PCC.

The use of phosphoric acid, $H_2PO_4^-$ or $HPO_4^{2-}$ as the $H_3O^+$ ion donor may lead to the formation of hydroxylapatite. Therefore, in a preferred embodiment, the at least one water-insoluble calcium salt is hydroxylapatite.

The amount of the at least one water-insoluble calcium salt present in the surface-reacted calcium carbonate may be quantified by XRD relative to the amount of calcite, aragonite and/or vaterite which is present in GNCC or PCC using the Rietveld method.

In a more preferred embodiment, the at least one water-insoluble calcium salt is hydroxylapatite, wherein the surface-reacted calcium carbonate provides a ratio of hydroxylapatite to calcite, aragonite and/or vaterite, preferably to calcite, in the range of from 1:99 to 99:1 by weight. Still more preferably, the surface-reacted calcium carbonate provides a ratio of hydroxylapatite to calcite, aragonite and/or vaterite, preferably to calcite, in the range of from 1:9 to 9:1, preferably 1:7 to 8:1, more preferably 1:5 to 7:1 and most preferably 1:4 to 7:1 by weight.

In a similar manner, the use of other $H_3O^+$ ion donors may lead to the formation of corresponding water-insoluble calcium salts other than calcium carbonate on at least part of the surface of the surface-reacted calcium carbonate. In one embodiment, the at least one water-insoluble calcium salt is thus selected from the group consisting of octacalcium phosphate, hydroxylapatite, chlorapatite, fluorapatite, carbonate apatite and mixtures thereof, wherein the surface-reacted calcium carbonate shows a ratio of the at least one water-insoluble calcium salt to calcite, aragonite and/or vaterite, preferably to calcite, in the range of from 1:99 to 99:1, preferably from 1:9 to 9:1, more preferably from 1:7 to 8:1, even more preferably from 1:5 to 7:1 and most preferably from 1:4 to 7:1 by weight.

As an alternative, it is also possible to add the $H_3O^+$ ion donor to the water before the natural or precipitated calcium carbonate is suspended.

In a next step, the natural or precipitated calcium carbonate is treated with $CO_2$. If a strong acid such as sulphuric acid or hydrochloric acid is used for the $H_3O^+$ ion donor treatment of the natural or precipitated calcium carbonate, the $CO_2$ is automatically formed. Alternatively or additionally, the $CO_2$ can be supplied from an external source.

$H_3O^+$ ion donor treatment and treatment with $CO_2$ can be carried out simultaneously which is the case when a strong or medium-strong acid is used. It is also possible to carry out $H_3O^+$ ion donor treatment first, e.g. with a medium strong acid having a $pK_a$ in the range of 0 to 2.5 at 20° C., wherein $CO_2$ is formed in situ, and thus, the $CO_2$ treatment will automatically be carried out simultaneously with the $H_3O^+$ ion donor treatment, followed by the additional treatment with $CO_2$ supplied from an external source.

Preferably, the concentration of gaseous $CO_2$ in the suspension is, in terms of volume, such that the ratio (volume of suspension): (volume of gaseous $CO_2$) is from 1:0.05 to 1:20, even more preferably 1:0.05 to 1:5.

In a preferred embodiment, the $H_3O^+$ ion donor treatment step and/or the $CO_2$ treatment step are repeated at least once, more preferably several times. According to one embodiment, the at least one $H_3O^+$ ion donor is added over a time period of at least about 5 min, preferably at least about 10 min, typically from about 10 to about 20 min, more preferably about 30 min, even more preferably about 45 min, and sometimes about 1 h or more.

Subsequent to the $H_3O^+$ ion donor treatment and $CO_2$ treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted natural or precipitated calcium carbonate as an aqueous suspension having a pH of greater than 6.0, preferably greater than 6.5, more preferably greater than 7.0, even more preferably greater than 7.5.

Further details about the preparation of the surface-reacted natural calcium carbonate are disclosed in WO 00/39222 A1, WO 2004/083316 A1, WO 2005/121257 A2, WO 2009/074492 A1, EP 2 264 108 A1, EP 2 264 109 A1 and US 2004/0020410 A1, the content of these references herewith being included in the present application.

Similarly, surface-reacted precipitated calcium carbonate may be obtained. As can be taken in detail from WO 2009/074492 A1, surface-reacted precipitated calcium carbonate is obtained by contacting precipitated calcium carbonate with $H_3O^+$ ions and with anions being solubilised in an aqueous medium and being capable of forming water-insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilised calcium ions correspond to an excess of solubilised calcium ions relative to the solubilised calcium ions naturally generated on dissolution of precipitated calcium carbonate by $H_3O^+$ ions, where said $H_3O^+$ ions are provided solely in the form of a counter ion to the anion, i.e. via the addition of the anion in the form of an acid or non-calcium acid salt, and in absence of any further calcium ion or calcium ion generating source.

Said excess solubilised calcium ions are preferably provided by the addition of a soluble neutral or acid calcium salt, or by the addition of an acid or a neutral or acid non-calcium salt which generates a soluble neutral or acid calcium salt in situ.

Said $H_3O^+$ ions may be provided by the addition of an acid or an acid salt of said anion, or the addition of an acid or an acid salt which simultaneously serves to provide all or part of said excess solubilised calcium ions.

In a further preferred embodiment of the preparation of the surface-reacted natural or precipitated calcium carbonate, the natural or precipitated calcium carbonate is reacted with the acid and/or the $CO_2$ in the presence of at least one compound selected from the group consisting of silicate, silica, aluminium hydroxide, earth alkali aluminate such as sodium or potassium aluminate, magnesium oxide, aluminium sulphate or mixtures thereof. Preferably, the at least one silicate is selected from an aluminium silicate, a calcium silicate, or an earth alkali metal silicate.

In another preferred embodiment, said at least one compound is aluminium sulphate hexadecahydrate. In a particularly preferred embodiment, said at least one compound is aluminium sulphate hexadecahydrate, wherein the at least one $H_3O^+$ ion donor is selected from the group consisting of hydrochloric acid, sulphuric acid, sulphurous acid, phosphoric acid, citric acid, oxalic acid, acetic acid, formic acid and mixtures thereof, more preferably the molar ratio of said $H_3O^+$ ion donor to the natural or precipitated calcium carbonate is from 0.01 to 4, more preferably from 0.02 to 2, even more preferably from 0.05 to 1 and most preferably from 0.1 to 0.58.

The foregoing components can be added to an aqueous suspension comprising the natural or precipitated calcium carbonate before adding the acid and/or $CO_2$.

Alternatively, the foregoing components can be added to the aqueous suspension of natural or precipitated calcium carbonate while the reaction of natural or precipitated calcium carbonate with an acid and $CO_2$ has already started. Further details about the preparation of the surface-reacted natural or precipitated calcium carbonate in the presence of at least one silicate and/or silica and/or aluminium hydroxide and/or earth alkali aluminate component(s) are disclosed in WO 2004/083316 A1, the content of this reference herewith being included in the present application.

The surface-reacted calcium carbonate can be kept in suspension, optionally further stabilised by a dispersant. Conventional dispersants known to the skilled person can be used. A preferred dispersant is comprised of polyacrylic acids and/or carboxymethylcelluloses.

Alternatively, the aqueous suspension described above can be dried, thereby obtaining the solid (i.e. dry or containing as little water that it is not in a fluid form) surface-reacted natural or precipitated calcium carbonate in the form of granules or a powder.

The surface reacted calcium carbonate may have different particle shapes, such as e.g. the shape of roses, golf balls and/or brains.

In a preferred embodiment, the surface-reacted calcium carbonate has a specific surface area of from 15 to 200 $m^2$/g, preferably from 27 to 180 $m^2$/g, more preferably from 25 to 160 $m^2$/g, even more preferably from 30 to 150 $m^2$/g, and most preferably from 48 to 140 $m^2$/g, measured using nitrogen and the BET method according to ISO 9277:2010. In a further embodiment, the surface-reacted calcium carbonate has a specific surface area of 120 $m^2$/g or less, more preferably from 60 to 120 $m^2$/g, and most preferably from 70 to 105 $m^2$/g, measured using nitrogen and the BET method according to ISO 9277:2010. For example, the surface-reacted calcium carbonate may have a specific surface area of from 75 to 100 $m^2$/g, measured using nitrogen and the BET method according to ISO 9277:2010.

It may furthermore be preferred that the surface-reacted calcium carbonate particles have a volume median grain diameter $d_{50}$(vol) of from 1 to 75 μm, preferably from 2 to 50 μm, more preferably from 3 to 40 μm, even more preferably from 4 to 30 μm, and most preferably from 5 to 15 μm. According to another preferred embodiment, the surface-reacted calcium carbonate particles have a volume median grain diameter $d_{50}$(vol) of from 1.5 to 12 μm, preferably from 2 to 5 μm or from 6 to 10 μm.

It may furthermore be preferred that the surface-reacted calcium carbonate particles have a grain diameter $d_{98}$(vol) of from 2 to 150 μm, preferably from 4 to 100 μm, more preferably from 6 to 80 μm, even more preferably from 8 to 60 μm, and most preferably from 10 to 30 μm. According to another preferred embodiment, the surface-reacted calcium carbonate particles have a volume median grain diameter $d_{98}$(vol) of from 5 to 20 μm, preferably from 8 to 12 μm or from 13 to 18 μm.

According to another embodiment, the surface-reacted calcium carbonate has an intra-particle intruded specific pore volume in the range from 0.1 to 2.3 $cm^3$/g, more preferably from 0.2 to 2.0 $cm^3$/g, especially preferably from 0.25 to 1.8 $cm^3$/g and most preferably from 0.3 to 1.6 $cm^3$/g, calculated from mercury porosimetry measurement.

The intra-particle pore size of the surface-reacted calcium carbonate preferably is in a range of from 0.004 to 1.6 μm, more preferably in a range of between 0.005 to 1.3 μm, especially preferably from 0.006 to 1.15 μm and most preferably of 0.007 to 1.0 μm, e.g. 0.004 to 0.50 μm determined by mercury porosimetry measurement.

As already indicated hereinabove, the specific pore volume can be measured using a mercury intrusion porosimetry measurement using a Micromeritics Autopore V 9620 mercury porosimeter.

For the purpose of step (a) of the present invention, the surface-reacted calcium carbonate may be provided either in dried form or as a suspension in a suitable liquid medium. Unless specified otherwise, the terms "dried" or "dry" refer to a material having constant weight at 150° C., whereby constant weight means a weight change of 1 mg or less over a period of 30 s per 5 g of sample.

In a preferred embodiment, the surface-reacted calcium carbonate is provided in form of a suspension in a liquid medium.

In case the surface-reacted calcium carbonate is provided in step (a) as a suspension or slurry, the suspension or slurry will contain a suitable liquid medium. Said liquid medium may differ from the liquid medium which is described hereinafter as a suitable liquid medium for the provision of the at least one transition metal compound in form of a solution or a suspension. However, in a preferred embodiment, the liquid medium for the provision of the at least one surface-reacted calcium carbonate and the liquid medium for the provision of the at least one transition metal compound is the same.

In general, said liquid medium may be a non-polar solvent, a polar solvent or a mixture thereof, preferably the non-polar solvent is selected from the group consisting of pentane, cyclopentane, hexane, cyclohexane, benzene, toluene, 1,4-dioxane, chloroform, diethyl ether, dichloromethane and mixtures thereof and/or the polar solvent is selected from the group consisting of tetrahydrofuran, ethyl acetate, acetone, dimethylformamide, acetonitrile, dimethyl sulphoxide, nitromethane, propylene carbonate, formic acid, n-butanol, isopropanol, n-propanol, ethanol, methanol, acetic acid, water and mixtures thereof. More preferably, the liquid medium is selected from water, ethanol, ethanol/water mixtures and toluene.

Said slurry may have a solids content within the range of from 1 to 90 wt.-%, preferably from 3 to 60 wt.-%, more preferably from 5 to 40 wt.-% and most preferably from 10 to 25 wt.-%, based on the total weight of the slurry.

Step (b): Providing at Least One Transition Metal Compound

In step (b) of the manufacturing method according to the present invention, at least one transition metal compound is provided.

A "transition metal" in the meaning of the present invention is any element in the d-block of the periodic table.

Preferably, the transition metal shows catalytic activity in chemical reactions. Thus, the transition metal may be selected from the following metals: titanium, chromium, manganese, iron, cobalt, copper, zinc, zirconium, molybdenum, ruthenium, palladium, silver, osmium, platinum, gold, mercury and mixtures thereof.

According to another preferred embodiment of the present invention, the transition metal is selected from copper, palladium, platinum and mixtures thereof, preferably palladium and platinum. In a particularly preferred embodiment, the transition metal is palladium.

The term "compound" in the meaning of the present invention shall include all kinds of chemical compounds which associate via chemical bonds including elemental forms, i.e. elemental transition metals which associate via metallic bonding.

In principle, there exist four types of compounds, depending on how the constituent atoms are held together: molecules held together by covalent bonds, salts held together by ionic bonds, intermetallic compounds held together by metallic bonds, and certain complexes held together by coordinate covalent bonds. The transition metal compound thus may be a molecular transition metal compound, a transition metal salt, a metallic transition metal compound including the elemental transition metal or a transition metal complex.

According to a preferred embodiment of the present invention, the transition metal compound is a transition metal salt or a transition metal complex.

In another preferred embodiment according to the present invention, the transition metal salt comprises one or more of the following counter ions: hydride, oxide, hydroxide, sulphide, fluoride, chloride, bromide, iodide, carbonate, acetate, cyanide, thiocyanate, nitrate, phosphate and sulphate.

In another preferred embodiment, the transition metal complex comprises one or more of the following ligands: acetylacetonate (acac), chloride, acetate, triphenylphosphine, 1,1'-bis(diphenylphosphino)ferrocene (dppf), 1,2-bis(diphenyl-phosphino)ethane (dppe), 1,3-bis(diphenylphosphino)propane (dppp), 1,4-bis-(diphenylphosphino)butane (dppb), allyl, dibenzylideneacetone or dibenzalacetone (dba), and ethylenediamine.

Therefore, according to another embodiment, the transition metal is an element in the d-block of the periodic table, preferably selected from titanium, chromium, manganese, iron, cobalt, copper, zinc, zirconium, molybdenum, ruthenium, palladium, silver, osmium, platinum, gold, mercury and mixtures thereof, and the transition metal compound is a molecular transition metal compound, a transition metal salt, a metallic transition metal compound including the elemental transition metal or a transition metal complex.

In a preferred embodiment, the transition metal is selected from titanium, chromium, manganese, iron, cobalt, copper, zinc, zirconium, molybdenum, ruthenium, palladium, silver, osmium, platinum, gold, mercury and mixtures thereof, preferably copper, palladium, platinum and mixtures thereof, more preferably palladium, platinum and mixtures thereof and most preferably palladium, and the transition metal compound is a transition metal salt or a transition metal complex. In a further preferred embodiment, the foregoing transition metal salt comprises one or more of the following counter ions: hydride, oxide, hydroxide, sulphide, fluoride, chloride, bromide, iodide, carbonate, acetate, cyanide, thiocyanate, nitrate, phosphate and sulphate and/or the foregoing transition metal complex comprises one or more of the following ligands: acac, chloride, acetate, triphenylphosphine, dppf, dppe, dppp, dppb, allyl, dba and ethylenediamine.

According to another embodiment, the transition metal compound is selected from elemental palladium, $Pd(acac)_2$, $Na_2PdCl_4$, $Pd(OAc)_2$, $Pd(PPh_3)_4$, $PdCl_2(PPh_3)_2$, (dppf)$PdCl_2$, (dppe)$PdCl_2$, (dppp)$PdCl_2$, (dppb)$PdCl_2$, $PdCl_2$, $(C_3H_5PdCO)_2$, bis(acetate)triphenylphosphine-palladium (II), $Pd(dba)_2$, $Pd(H_2NCH_2CH_2NH_2)Cl_2$, elemental platinum, $Na_2PtCl_6$, $Pt(acac)_2$, $Na_2PtCl_4$, $H_2PtCl_6$, $(NH_4)_2[PtCl_6]$, $PtO_2 \cdot H_2O$, $PtCl_4$, elemental copper, $Cu_2O$, $Cu_2S$, copper(I)-thiophene-2-carboxylate, CuBr, CuCN, CuCl, CuF, CuI, CuH, CuSCN, $CuBr_2$, $CuCO_3$, $CuCl_2$, $CuF_2$, $Cu(NO_3)_2$, $Cu_3(PO_4)_2$, CuO, $CuO_2$, $Cu(OH)_2$, Cub, CuS, $CuSO_4$, $Cu_2(OAc)_4$ and mixtures thereof, preferably the transition metal compound is selected from the group consisting of elemental palladium, $Pd(acac)_2$, $Na_2PdCl_4$, $Pd(OAc)_2$, $Pd(PPh_3)_4$, $PdCl_2(PPh_3)_2$, (dppf)$PdCl_2$, (dppe)$PdCl_2$, (dppp)$PdCl_2$, (dppb)$PdCl_2$, $PdCl_2$, $(C_3H_5PdCO)_2$, bis(acetate)triphenylphosphine-palladium(II), $Pd(dba)_2$, $Pd(H_2NCH_2CH_2NH_2)Cl_2$, elemental platinum, $Na_2PtCl_6$ $Pt(acac)_2$, $Na_2PtCl_4$, $H_2PtCl_6$, $(NH_4)_2[PtCl_6]$, $PtO_2 \cdot H_2O$, $PtCl_4$ and mixtures thereof.

According to still another embodiment of the present invention, the transition metal compound is selected from $Pd(acac)_2$, $Pt(acac)_2$, $Na_2PdCl_4$, $Na_2PtCl_4$ and mixtures thereof, preferably $Pd(acac)_2$, $Pt(acac)_2$ and more preferably the transition metal compound is $Pd(acac)_2$.

For the purpose of step (b), the transition metal compound may in principle be provided in any form, meaning that the transition metal compound may be provided as a neat compound or it may be provided in a liquid medium in form of a solution or suspension.

The provision in a liquid medium may be preferred as this may lead to a more homogenous mixture in any of the subsequent steps, for example in contacting step (c) of the inventive method for manufacturing the catalyst system. For the same reason, solutions may be preferred over suspensions. In a preferred embodiment, the transition metal compound in step (b) is thus provided in a liquid medium in form of a solution or suspension, preferably in form of a solution.

In general, it is possible to use protic and aprotic solvents or polar and non-polar solvents. Non-limiting examples of suitable liquid media thus include water, ethanol and $C_{3-5}$ alkyl alcohols, acetone, tetrahydrofuran, acetonitrile, dimethylsulphoxide, dimethylformamide, chloroform, dichloromethane, ethyl acetate, diethyl ether, methyl tent-butyl ether, benzene, toluene and mixtures thereof. The skilled person will know how to select suitable solvents and mixtures thereof.

In a preferred embodiment, the transition metal compound is thus selected from the group consisting of palladium compounds, platinum compounds, copper compounds and mixtures thereof, preferably the transition metal compound is a transition metal salt or a transition metal complex and more preferably the transition metal compound is $Pd(acac)_2$ and/or $Pt(acac)_2$, wherein the transition metal compound in step (b) is provided in a liquid medium in form of a solution or suspension, preferably in form of a solution.

According to another embodiment, the liquid medium is a non-polar solvent, a polar solvent or a mixture thereof, preferably the non-polar solvent is selected from the group consisting of pentane, cyclopentane, hexane, cyclohexane, benzene, toluene, 1,4-dioxane, chloroform, diethyl ether, dichloromethane and mixtures thereof and/or the polar solvent is selected from the group consisting of tetrahydrofuran, ethyl acetate, acetone, dimethylformamide, acetonitrile, dimethyl sulphoxide, nitromethane, propylene carbonate, formic acid, n-butanol, isopropanol, n-propanol, ethanol, methanol, acetic acid, water and mixtures thereof.

According to still another embodiment of the present invention, the liquid medium is selected from water, ethanol, ethanol/water mixtures and toluene.

According to still another embodiment, the transition metal is selected from titanium, chromium, manganese, iron, cobalt, copper, zinc, zirconium, molybdenum, ruthenium, palladium, silver, osmium, platinum, gold, mercury and mixtures thereof, wherein the transition metal compound is a transition metal salt or a transition metal complex and wherein the transition metal compound is provided in a liquid medium in form of a solution or suspension, preferably in form of a solution. In a further preferred embodiment, the foregoing transition metal salt comprises one or more of the following counter ions: hydride, oxide, hydroxide, sulphide, fluoride, chloride, bromide, iodide, carbonate, acetate, cyanide, thiocyanate, nitrate, phosphate and sulphate and/or the foregoing transition metal complex comprises one or more of the following ligands: acac, chloride, acetate, triphenylphosphine, dppf, dppe, dppp, dppb, allyl, dba and ethylenediamine.

According to still another embodiment, the transition metal compound is selected from the group consisting of palladium compounds, platinum compounds, copper compounds and mixtures thereof, preferably the transition metal compound is a transition metal salt or a transition metal complex and more preferably the transition metal compound is selected from the group consisting of elemental palladium, $Pd(acac)_2$, $Na_2PdCl_4$, $Pd(OAc)_2$, $Pd(PPh_3)_4$, $PdCl_2(PPh_3)_2$, $(dppf)PdCl_2$, $(dppe)PdCl_2$, $(dppp)PdCl_2$, $(dppb)PdCl_2$, $PdCl_2$, $(C_3H_5PdCl)_2$, bis(acetate)triphenylphosphine-palladium(II), $Pd(dba)_2$, $Pd(H_2NCH_2CH_2NH_2)Cl_2$, elemental platinum, $Na_2PtCl_6$ $Pt(acac)_2$, $Na_2PtCl_4$,$H_2PtCl_6$, $(NH_4)_2[PtCl_6]$, $PtO_2.H_2O$, $PtCl_4$, elemental copper, $Cu_2O$, $Cu_2S$, copper(I)-thiophene-2-carboxylate, CuBr, CuCN, CuCl, CuF, CuI, CuH, CuSCN, $CuBr_2$, $CuCO_3$, $CuCl_2$, $CuF_2$, $Cu(NO_3)_2$, $Cu_3(PO_4)_2$, CuO, $CuO_2$, $Cu(OH)_2$, $CuI_2$, CuS, $CuSO_4$, $Cu_2(OAc)_4$ and mixtures thereof, preferably the transition metal compound is selected from the group consisting of elemental palladium, $Pd(acac)_2$, $Na_2PdCl_4$, $Pd(OAc)_2$, $Pd(PPh_3)_4$, $PdCl_2(PPh_3)_2$, $(dppf)PdCl_2$, $(dppe)PdCl_2$, $(dppp)PdCl_2$, $(dppb)PdCl_2$, $PdCl_2$, $(C_3H_5PdCl)_2$, bis(acetate)triphenyl-phosphine-palladium(II), $Pd(dba)_2$, $Pd(H_2NCH_2CH_2NH_2)Cl_2$, elemental platinum, $Na_2PtCl_6$ $Pt(acac)_2$, $Na_2PtCl_4$, $H_2PtCl_6$, $(NH_4)_2[PtCl_6]$, $PtO_2.H_2O$, $PtCl_4$ and mixtures thereof, wherein the transition metal compound is provided in a liquid medium in form of a solution or suspension, preferably in form of a solution and wherein the liquid medium is an organic solvent, preferably toluene, or the liquid medium is an aqueous solvent, preferably water, or the liquid medium is a mixture of an organic solvent and water, preferably a mixture of ethanol and water.

According to a preferred embodiment, the transition metal compound is selected from the group consisting of palladium compounds, platinum compounds, copper compounds and mixtures thereof, preferably the transition metal compound is a transition metal salt or a transition metal complex and more preferably the transition metal compound is $Pd(acac)_2$ and/or $Pt(acac)_2$, wherein the liquid medium is an organic solvent, preferably benzene or toluene, more preferably toluene.

According to another preferred embodiment, the transition metal compound is selected from the group consisting of palladium compounds, platinum compounds, copper compounds and mixtures thereof, preferably the transition metal compound is a transition metal salt or a transition metal complex and more preferably the transition metal compound is $Na_2PdCl_4$ and/or $Na_2PtCl_4$, wherein the liquid medium is an aqueous solvent, preferably water.

The amount of transition metal compound provided in step (b) may vary and may be adjusted to the specific needs. According to one embodiment of the present invention, the amount of the transition metal compound provided in step (b) is in the range of from 0.1 to 20 wt.-%, preferably from 0.1 to 10 wt.-% and more preferably 0.2 to 5 wt.-%, based on the weight of the transition metal per total weight of the surface-reacted calcium carbonate.

The skilled person will appreciate that the transition metal compound provided in step (b) may at least partially be subject to a chemical transformation during any of the subsequent steps (c)-(e). In one embodiment, one or more reaction products obtained by reaction of the transition metal compound and the surface-reacted calcium carbonate may thus be present in the mixture obtained in step (c) and/or in the concentrated mixture obtained in step (e) and/or in the product obtained in step (e).

Step (c): Contacting the Surface-Reacted Calcium Carbonate qnd the Transition Metal Compound In step (c) of the manufacturing method according to the present invention, the surface-reacted calcium carbonate provided in step (a) and the transition metal compound provided in step (b) are brought into contact in a liquid medium to obtain a mixture comprising surface-reacted calcium carbonate and a transition metal compound.

Step (c) of contacting the surface-reacted calcium carbonate and the transition metal compound serves to impregnate at least part of the accessible surface of the surface-reacted calcium carbonate with said transition metal compound to provide a catalyst system with a transition metal compound on a solid carrier.

The contacting of the at least one surface-reacted calcium carbonate provided in step (a) and the at least one transition metal compound provided in step (b) can be accomplished by any conventional means known to the skilled person.

According to one embodiment of the present invention, step (c) comprises the steps of providing the at least one surface-reacted calcium carbonate provided in step (a) in a first step and then adding the at least one transition metal compound provided in step (b) in a subsequent step. According to another embodiment of the present invention, step (c) comprises the steps of first providing the at least one transition metal compound provided in step (b) and subsequently adding the at least one surface-reacted calcium carbonate provided in step (a). According to still another embodiment, the at least one surface-reacted calcium carbonate provided in step (a) and the at least one transition metal compound provided in step (b) are provided and contacted simultaneously.

In case the at least one surface-reacted calcium carbonate provided in step (a) is provided as a first step, it is possible to add the at least one transition metal compound provided in step (b) in one portion or it may be added in several equal or unequal portions, i.e. in larger and smaller portions.

During contacting step (c) of the inventive process, a mixture comprising the surface-reacted calcium carbonate of step (a) and the transition metal compound of step (b) is obtained. Said mixture may be a suspension or slurry in a liquid medium.

In one embodiment of the process according to the present invention (i) the at least one surface-reacted calcium carbonate of step (a) is provided in a liquid medium in form of a suspension; and/or (ii) the at least one transition metal compound of step (b) is provided in a liquid medium in form of a solution or a suspension, preferably in form of a solution.

In a preferred embodiment, the surface-reacted calcium carbonate is provided as a suspension in a liquid medium, wherein also the transition metal compound is provided in a liquid medium in form of a solution or suspension, preferably in form of a solution.

As already described hereinabove, the surface-reacted calcium carbonate may be provided in step (a) as a suspension or slurry, in which case the suspension or slurry will contain a suitable liquid medium. In general, said liquid medium may differ from the liquid medium described herein as a suitable liquid medium for the provision of the at least one transition metal compound in step (b) in form of a solution or a suspension.

However, in a preferred embodiment, the liquid medium for the provision of the at least one surface-reacted calcium carbonate and the liquid medium for the provision of the at least one transition metal compound is the same.

The mixture obtained in step (c) may comprise any of the liquid media disclosed hereinabove, for example the liquid medium may be a non-polar solvent, a polar solvent or a mixture thereof, preferably the non-polar solvent is selected from the group consisting of pentane, cyclopentane, hexane, cyclohexane, benzene, toluene, 1,4-dioxane, chloroform, diethyl ether, dichloromethane and mixtures thereof and/or the polar solvent is selected from the group consisting of tetrahydrofuran, ethyl acetate, acetone, dimethylformamide, acetonitrile, dimethyl sulphoxide, nitromethane, propylene carbonate, formic acid, n-butanol, isopropanol, n-propanol, ethanol, methanol, acetic acid, water and mixtures thereof. Preferably, the mixture obtained in step (c) further comprises water, ethanol, ethanol/water mixtures, toluene and mixtures thereof.

The contacting step (c) can be carried out by any means known in the art. For example, the at least one surface-reacted calcium carbonate of step (a) and the transition metal compound of step (b) can be brought into contact by spraying and/or mixing. Suitable devices for spraying or mixing are known to the skilled person.

According to one embodiment of the present invention, step (c) may be carried out by spraying. Preferably, step (c) is carried out by mixing.

The mixing in step (c) can be accomplished by any conventional means known to the skilled person. The skilled person will adapt the mixing conditions such as the mixing speed, dividing, and temperature according to his process equipment. Additionally, the mixing may be carried out under homogenising and/or particle dividing conditions.

For example, mixing and homogenising may be performed by use of a ploughshare mixer. Ploughshare mixers function by the principle of a fluidised bed which is produced mechanically. Ploughshare blades rotate close to the inside wall of a horizontal cylindrical drum, thereby conveying the components of the mixture out of the product bed and into the open mixing space. Said fluidised bed ensures intense mixing of even large batches in a very short time. Choppers and/or dispersers are used to disperse lumps in case of a dry operating mode. Equipment that may be used in the inventive process is commercially available, for example, from Gebrüder Lodige Maschinenbau GmbH, Germany or from VISCO JET Rührsysteme GmbH, Germany.

According to another embodiment of the present invention, step (c) is carried out for at least 1 second, preferably for at least 1 minute (e.g. 10 min, 30 min or 60 min). According to a preferred embodiment step (c) is carried out for a period of time ranging from 1 second to 60 min, preferably for a period of time ranging from 15 min to 45 min. For example, mixing step (d) is carried out for 30 min±5 min.

It is also within the confines of the present invention that suitable liquid medium as described hereinabove may be added during process step (c), for example, in case the surface-reacted calcium carbonate is provided in dry form and the transition metal compound is provided in neat form or in case it is intended to adjust the solids content or the Brookfield viscosity of the mixture to a specific value.

According to one embodiment of the present invention, the mixture obtained in step (c) has a solids content within the range of from 1 to 90 wt.-%, preferably from 3 to 60 wt.-%, more preferably from 5 to 40 wt.-% and most preferably from 10 to 25 wt.-%, based on the total weight of said mixture.

Step (d): Removing the Liquid Medium

The method according to the present invention may optionally comprise step (d) of removing liquid medium from the mixture obtained in step (c).

As already discussed hereinabove, the mixture obtained in contacting step (c) may comprise a liquid medium, for example if the at least one surface-reacted calcium carbonate in step (a) is provided as a suspension or slurry or if the at least one transition metal compound in step (b) is provided in form of a solution or suspension. Further to this, the mixture obtained in contacting step (c) may comprise a liquid medium to be removed in step (d) if said liquid medium is added during contacting step (c), for example to adjust the solids content of said mixture.

Step (d) yields a concentrated mixture which contains less liquid medium than the mixture obtained in contacting step (c). In principle, concentrating step (d) can be accomplished by any conventional means known to the skilled person, for example by evaporation of the liquid medium or by filtration.

Therefore, in one embodiment according to the present invention, at least part of the liquid medium contained in the mixture of step (c) is removed by evaporation and/or by filtration.

The method of choice in step (d) may depend on the nature of the liquid medium contained in the mixture of step (c). For example, it may be preferred to remove aprotic solvents (e.g. toluene) by evaporation while protic solvents (e.g. ethanol or water) may preferably be removed by filtration. In further instances, an initial filtration combined with subsequent evaporation of residual liquid medium under reduced pressure (vacuum) may be preferred.

According to one embodiment of the present invention, the inventive process further comprises step (d) of removing at least part of the liquid medium contained in the mixture of step (c) by evaporation. For example, evaporation of the liquid medium may be carried out by application of heat and/or reduced pressure in an evaporator.

According to another embodiment of the present invention, the inventive process further comprises step (d) of removing at least part of the liquid medium contained in the mixture of step (c) by filtration. For example, filtration may be carried out by means of a drum filter or a filter press or by means of nanofiltration.

According to still another embodiment of the present invention, the inventive process further comprises step (d) of removing at least part of the liquid medium contained in the mixture of step (c) by filtration and evaporation, preferably by filtration and subsequent evaporation.

The concentrated mixture obtained in step (d), after removing at least part of the liquid medium contained in the mixture of step (c), is a concentrated mixture. In a preferred embodiment, said concentrated mixture has a solids content of at least 70 wt.-%, preferably at least 80 wt.-%, more preferably at least 85 wt.-% and most preferably at least 90 wt.-%, based on the total weight of said mixture. For example, said concentrated mixture may have a solids content of 95 wt.-%, based on the total weight of said mixture.

According to still another embodiment of the inventive process, the liquid medium contained in the mixture of step (c) is removed in step (d) to obtain a dried mixture.

Step (e): Thermal Treatment

According to step (e) of the method for manufacturing the inventive catalyst system, the mixture of step (c) or the concentrated mixture of optional step (d) is thermally treated at a temperature of below 400° C., preferably in the range from 170° C. to 400° C., more preferably from 200° C. to 300° C., even more preferably from 250 to 310° C. and most preferably from 280° C. to 320° C.

The term "heating" is not limiting the process according to the present invention to a process, wherein the temperature of the mixture is adjusted actively to the defined temperature range by addition of energy through an external heat source. Said term also comprises keeping the temperature reached in an exothermic reaction, for example in contacting step (c), during a specified period of time.

It is believed that the thermal treatment carried out in step (e) may further improve the performance of the catalyst system. For example, further improvements may be observed with regard to the catalytic activity, turnover rates or product yields. Yet further improvements may be observed, for example, with regard to the recovery of the inventive catalyst system and the recycling in a second or further catalytic cycle.

The foregoing advantages may be particularly pronounced if the thermal treatment is carried out for a specific period of time. In one embodiment, step (e) is thus carried out for at least 10 min, preferably for 0.5 h to 24 h, more preferably for 1 h to 5 h and most preferably for 2.5 to 3.5 h.

In a preferred embodiment, the mixture of step (c) or the concentrated mixture of optional step (d) is thermally treated at a temperature of below 400° C., preferably in the range from 170° C. to 400° C., more preferably from 200° C. to 300° C., even more preferably from 250 to 310° C. and most preferably from 280° C. to 320° C., wherein said thermal treatment is carried out for at least 10 min, preferably for 0.5 h to 24 h, more preferably for 1 h to 5 h and most preferably for 2.5 to 3.5 h.

The Catalyst System

The catalyst system according to the present invention comprises a transition metal compound on a solid carrier, wherein the solid carrier is a surface-reacted calcium carbonate comprising ground natural calcium carbonate (GNCC) or precipitated calcium carbonate (PCC), and at least one water-insoluble calcium salt other than calcium carbonate. Said surface-reacted calcium carbonate is a reaction product of ground natural calcium carbonate (GNCC) or precipitated calcium carbonate (PCC) treated with $CO_2$ and one or more $H_3O^+$ ion donors and wherein the $CO_2$ is formed in situ by the $H_3O^+$ ion donors treatment and/or is supplied from an external source.

In general, the inventive catalyst system is composed of a particulate solid carrier material (surface-reacted calcium carbonate) with a transition metal compound present on at least part of the accessible surface of said carrier material.

Specific embodiments of the surface-reacted calcium carbonate are already described hereinabove under step (a) of the inventive process and shall apply accordingly to the surface-reacted calcium carbonate of the inventive catalyst system.

For example, the use of phosphoric acid, $H_2PO_4^-$ or $HPO_4^{2-}$ as the $H_3O^+$ ion donor may lead to the formation of hydroxylapatite. Therefore, in a preferred embodiment, the at least one water-insoluble calcium salt is hydroxylapatite.

In a more preferred embodiment, the at least one water-insoluble calcium salt is hydroxylapatite, wherein the surface-reacted calcium carbonate provides a ratio of hydroxylapatite to calcite, aragonite and/or vaterite, preferably to calcite, in the range of from 1:99 to 99:1 by weight. Still more preferably, the surface-reacted calcium carbonate provides a ratio of hydroxylapatite to calcite, aragonite and/or vaterite, preferably to calcite, in the range of from 1:9 to 9:1, preferably 1:7 to 8:1, more preferably 1:5 to 7:1 and most preferably 1:4 to 7:1 by weight.

In a similar manner, the use of other $H_3O^+$ ion donors may lead to the formation of corresponding water-insoluble calcium salts other than calcium carbonate on at least part of the surface of the surface-reacted calcium carbonate. In one embodiment, the at least one water-insoluble calcium salt is thus selected from the group consisting of octacalcium phosphate, hydroxylapatite, chlorapatite, fluorapatite, carbonate apatite and mixtures thereof, wherein the surface-reacted calcium carbonate shows a ratio of the at least one water-insoluble calcium salt to calcite, aragonite and/or vaterite, preferably to calcite, in the range of from 1:99 to 99:1, preferably from 1:9 to 9:1, more preferably from 1:7 to 8:1, even more preferably from 1:5 to 7:1 and most preferably from 1:4 to 7:1 by weight.

The catalyst system according to the present invention further comprises a transition metal compound. Specific embodiments of said transition metal compound are also described hereinabove under step (b) and shall apply accordingly to the transition metal compound of the catalyst system.

In one exemplary embodiment, a catalyst system comprising a transition metal compound on a solid carrier is provided, wherein the solid carrier is a surface-reacted calcium carbonate comprising ground natural calcium carbonate (GNCC) or precipitated calcium carbonate (PCC), and at least one water-insoluble calcium salt other than calcium carbonate, and wherein the surface-reacted calcium carbonate shows:
  (i) a specific surface area of from 15 to 200 m$^2$/g measured using nitrogen and the BET method according to ISO 9277:2010;
  (ii) an intra-particle intruded specific pore volume in the range of from 0.1 to 2.3 cm$^3$/g calculated from mercury porosimetry measurement; and
  (iii) a ratio of the at least one water-insoluble calcium salt to calcite, aragonite and/or vaterite in the range of from 1:99 to 99:1 by weight.

In another exemplary embodiment, the catalyst system according to the present invention thus comprises a transition metal compound on a solid carrier, wherein the solid carrier is a surface-reacted calcium carbonate which is a reaction product of ground natural calcium carbonate (GNCC) or precipitated calcium carbonate (PCC) treated with $CO_2$ and one or more $H_3O^+$ ion donors, wherein the $CO_2$ is formed in situ by the $H_3O^+$ ion donors treatment and/or is supplied from an external source, said surface-reacted calcium carbonate comprising ground natural calcium carbonate (GNCC) or precipitated calcium carbonate (PCC), and at least one water-insoluble calcium salt other than calcium carbonate, and wherein the surface-reacted calcium carbonate has:
  (i) a specific surface area of from 15 to 200 $m^2/g$ measured using nitrogen and the BET method according to ISO 9277:2010;
  (ii) an intra-particle intruded specific pore volume in the range of from 0.1 to 2.3 $cm^3/g$ calculated from mercury porosimetry measurement; and
  (iii) a ratio of the at least one water-insoluble calcium salt to calcite, aragonite and/or vaterite in the range of from 1:99 to 99:1 by weight.

According to still another exemplary embodiment, a catalyst system comprising a transition metal compound on a solid carrier is provided, wherein the solid carrier is a surface-reacted calcium carbonate comprising ground natural calcium carbonate (GNCC) or precipitated calcium carbonate (PCC), and at least one water-insoluble calcium salt other than calcium carbonate, wherein the surface-reacted calcium carbonate shows:
  (i) a specific surface area of from 15 to 200 $m^2/g$ measured using nitrogen and the BET method according to ISO 9277:2010;
  (ii) an intra-particle intruded specific pore volume in the range of from 0.1 to 2.3 $cm^3/g$ calculated from mercury porosimetry measurement; and
  (iii) a ratio of the at least one water-insoluble calcium salt to calcite, aragonite and/or vaterite in the range of from 1:99 to 99:1 by weight. and wherein the transition metal compound is selected from the group consisting of palladium compounds, platinum compounds, copper compounds and mixtures thereof, preferably the transition metal compound is a transition metal salt or a transition metal complex.

According to still another exemplary embodiment, the catalyst system according to the present invention thus comprises a transition metal compound on a solid carrier, wherein the solid carrier is a surface-reacted calcium carbonate which is a reaction product of ground natural calcium carbonate (GNCC) or precipitated calcium carbonate (PCC) treated with $CO_2$ and one or more $H_3O^+$ ion donors, wherein the $CO_2$ is formed in situ by the $H_3O^+$ ion donors treatment and/or is supplied from an external source, said surface-reacted calcium carbonate comprising ground natural calcium carbonate (GNCC) or precipitated calcium carbonate (PCC), and at least one water-insoluble calcium salt other than calcium carbonate, wherein the surface-reacted calcium carbonate has:
  (i) a specific surface area of from 15 to 200 $m^2/g$ measured using nitrogen and the BET method according to ISO 9277:2010;
  (ii) an intra-particle intruded specific pore volume in the range of from 0.1 to 2.3 $cm^3/g$ calculated from mercury porosimetry measurement; and
  (iii) a ratio of the at least one water-insoluble calcium salt to calcite, aragonite and/or vaterite in the range of from 1:99 to 99:1 by weight;

and wherein the transition metal compound is selected from the group consisting of palladium compounds, platinum compounds, copper compounds and mixtures thereof, preferably the transition metal compound is a transition metal salt or a transition metal complex.

In any of the foregoing exemplary embodiments, the transition metal compound may be preferably selected from the group consisting of elemental palladium, $Pd(acac)_2$, $Na_2PdCl_4$, $Pd(OAc)_2$, $Pd(PPh_3)_4$, $PdCl_2(PPh_3)_2$, $(dppf)PdCl_2$, $(dppe)PdCl_2$, $(dppp)PdCl_2$, $(dppb)PdCl_2$, $PdCl_2$, $(C_3H_5PdCl)_2$, bis(acetate)triphenylphosphine-palladium(II), $Pd(dba)_2$, $Pd(H_2NCH_2CH_2NH_2)Cl_2$, elemental platinum, $Na_2PtCl_6 Pt(acac)_2$, $Na_2PtCl_4$, $H_2PtCl_6$, $(NH_4)_2[PtCl_6]$, $PtO_2.H_2O$, $PtCl_4$, elemental copper, $Cu_2O$, $Cu_2S$, copper(I)-thiophene-2-carboxylate, CuBr, CuCN, CuCl, CuF, CuI, CuH, CuSCN, $CuBr_2$, $CuCO_3$, $CuCl_2$, $CuF_2$, $Cu(NO_3)_2$, $Cu_3(PO_4)_2$, CuO, $CuO_2$, $Cu(OH)_2$, $CuI_2$, CuS, $CuSO_4$, $Cu_2(OAc)_4$ and mixtures thereof, preferably the transition metal compound is selected from the group consisting of elemental palladium, $Pd(acac)_2$, $Na_2PdCl_4$, $Pd(OAc)_2$, $Pd(PPh_3)_4$, $PdCl_2(PPh_3)_2$, $(dppf)PdCl_2$, $(dppe)PdCl_2$, $(dppp)PdCl_2$, $(dppb)PdCl_2$, $PdCl_2$, $(C_3H_5PdCl)_2$, bis(acetate)triphenylphosphine-palladium(II), $Pd(dba)_2$, $Pd(H_2NCH_2CH_2NH_2)Cl_2$, elemental platinum, $Na_2PtCl_6$ $Pt(acac)_2$, $Na_2PtCl_4$, $H_2PtCl_6$, $(NH_4)_2[PtCl_6]$, $PtO_2.H_2O$, $PtCl_4$ and mixtures thereof.

The skilled person will appreciate that the transition metal compound provided in step (b) may at least partially be subject to a chemical transformation during any of the subsequent steps (c)-(e). In one embodiment, one or more reaction products obtained by reaction of the transition metal compound and the surface-reacted calcium carbonate may thus be present in the mixture obtained in step (c) and/or in the concentrated mixture obtained in step (e) and/or in the product obtained in step (e).

Accordingly, in one embodiment, also the catalyst system further comprises one or more reaction products obtained by reaction of the transition metal compound and the surface-reacted calcium carbonate. In a preferred embodiment of the present invention, said one or more reaction products include hydrogen carbonates, carbonates, hydroxides and oxides of the said transition metal as well as elemental forms of said transition metal.

The content of the transition metal compound and/or the one or more reaction products thereof may be in the range of from 0.1 to 60 wt.-%, preferably from 0.1 to 30 wt.-%, more preferably 0.1 to 20 wt.-%, even more preferably from 0.1 to 10 wt.-% and most preferably from 0.2 to 5 wt.-%, based on the weight of the transition metal compound per total weight of the catalyst system.

Use of the Inventive Catalyst System in Heterogeneous Catalysis

The inventive catalyst system was found to be particularly useful in a number of catalytic reactions. For example, higher conversion rates in C—C cross coupling reactions and higher yields in glycerol hydrogenolysis were achieved.

One aspect of the present application therefore relates to the use of the inventive catalyst system in a process comprising the following steps:
  (a) providing one or more reactants;
  (b) providing the inventive catalyst system;
  (c) subjecting the one or more reactants provided in step (a) to a chemical reaction in the presence of the catalyst system provided in step (b).

As it was found that the inventive catalyst system can be recovered more easily and higher yields can be achieved in a second catalytic cycle compared with conventional carrier systems, a preferred embodiment of the present invention relates to the use of the inventive catalyst system in a process according to the foregoing aspect, wherein said process further comprises step (d) of recovering the catalyst system following the chemical reaction of step (c) and recycling the transition metal. It is to be understood that the term "recycling" encompasses recycling of the transition metal in any form which includes recycling of the complete catalyst system.

In a preferred embodiment of the present invention, the chemical reaction in step (c) comprises heterogeneous catalysis. In a more preferred embodiment, the chemical reaction in step (c) may be selected from one or more of the following reaction types: hydrogenolyses, C—C couplings and C—C cross couplings, C—N cross couplings, C—O cross couplings, C—S cross couplings, cycloaddition reactions, alkene hydrogenations and alkyne hydrogenations, allylic substitutions, reductions of nitro groups and hydrocarbonylations of aryl halides, preferably hydrogenolyses, C—C couplings and C—C cross couplings.

The inventive catalyst system may also be used in form of granules, mouldings or extrudates comprising said catalyst system. Typical shapes include spheres, minispheres, miniliths, honeycombs, rings etc.

Granules are made by crushing and screening gels to obtain the desired size or by drying precipitated pastes together with binders. Optionally, the granulation process further includes heat treatment to achieve specific physical properties. The particle size of granules typically ranges from 40 μm up to 1 cm.

Mouldings are hollow forms having a particular shape obtained from something in a malleable state.

Extrudates are formed by pushing a paste through a die, cutting to length, drying and optional calcining.

EXAMPLES

A) Analytical Methods

The parameters defined throughout the present application and determined in the following examples are based on the following measuring methods:

Solids Content

The suspension solids content (also known as "dry weight") is determined using a Moisture Analyser MJ33 (Mettler-Toledo, Switzerland), with the following settings: drying temperature of 150° C., automatic switch off if the mass does not change more than 1 mg over a period of 30 s, standard drying of 5 g of suspension.

Particle Size Distribution of a Particulate Material

The particle size of surface-reacted calcium carbonate herein is described as volume-based particle size distribution $d_x(vol)$. The volume determined median particle size $d_{50}$ (vol) and the volume determined top cut particle size $d_{98}$ (vol) were evaluated using a Malvern Mastersizer 2000 Laser Diffraction System (Malvern Instruments Plc., Great Britain). The $d_{50}(vol)$ or $d_{98}(vol)$ value indicates a diameter value such that 50% or 98% by volume, respectively, of the particles have a diameter of less than this value. The raw data obtained by the measurement was analyzed using the Mie theory, with a particle refractive index of 1.57 and an absorption index of 0.005. The methods and instruments are known to the skilled person and are commonly used to determine particle size distributions of fillers and pigments.

The particle size of particulate materials other than surface-reacted calcium carbonate is described herein as weight-based particle size distribution $d_x(vol)$. The weight determined median particle size $d_{50}(wt)$ was measured by the sedimentation method, which is an analysis of sedimentation behaviour in a gravimetric field. The measurement was made with a Sedigraph™ 5100 or 5120 of Micromeritics Instrument Corporation, USA. The method and the instrument are known to the skilled person and are commonly used to determine particle size distributions of fillers and pigments. The measurement was carried out in an aqueous solution of 0.1 wt.-% $Na_4P_2O_7$. The samples were dispersed using a high speed stirrer and supersonicated.

Porosimetry

The specific pore volume is measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 μm (~nm). The equilibration time used at each pressure step is 20 s. The sample material is sealed in a 3 $cm^3$ chamber powder penetrometer for analysis. The data are corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p 1753-1764.).

The total pore volume seen in the cumulative intrusion data can be separated into two regions with the intrusion data from 214 μm down to about 1 to 4 μm showing the coarse packing of the sample between any agglomerate structures contributing strongly. Below these diameters lies the fine interparticle packing of the particles themselves. If they also have intraparticle pores, then this region appears bimodal, and by taking the specific pore volume intruded by mercury into pores finer than the modal turning point, i.e. finer than the bimodal point of inflection, we thus define the specific intraparticle pore volume. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the interparticle pore region and the intraparticle pore region, if present. Knowing the intraparticle pore diameter range it is possible to subtract the remainder interparticle and interagglomerate pore volume from the total pore volume to deliver the desired pore volume of the internal pores alone in terms of the pore volume per unit mass (specific pore volume). The same principle of subtraction, of course, applies for isolating any of the other pore size regions of interest.

BET Specific Surface Area (SSA) of a Material

Throughout the present document, the specific surface area (in $m^2/g$) of surface-reacted calcium carbonate or other materials is determined using the BET method (using nitrogen as adsorbing gas), which is well known to the skilled man (ISO 9277:2010). The total surface area (in $m^2$) of the filler material is then obtained by multiplication of the specific surface area and the mass (in g) of treatment corresponding sample.

X-Ray Diffraction (XRD)

XRD experiments are performed on the samples using rotatable PMMA holder rings. Samples are analysed with a Bruker D8 Advance powder diffractometer obeying Bragg's law. This diffractometer consists of a 2.2 kW X-ray tube, a sample holder, a ϑ-ϑ-goniometer, and a VANTEC-1 detector. Nickel-filtered Cu Kα radiation is employed in all experiments. The profiles are chart recorded automatically using a scan speed of 0.7° per min in 2θ. The resulting powder diffraction pattern can easily be classified by mineral content using the DIFFRACsuite software packages EVA and SEARCH, based on reference patterns of the ICDD PDF 2 database.

Quantitative analysis of diffraction data refers to the determination of amounts of different phases in a multi-phase sample and has been performed using the DIFFRACsuite software package TOPAS. In detail, quantitative analysis allows to determine structural characteristics and phase proportions with quantifiable numerical precision from the experimental data itself. This involves modelling the full diffraction pattern using the Rietveld approach such that the calculated pattern(s) duplicates the experimental one.

HPLC Chromatography

Suzuki reaction: Samples were analysed on a Waters Symmetry Shield™ column (RP-8, 3.5 µM, 4.6×50 mM) using a Dionex P680 HPLC pump (1.0 ml·min$^{-1}$) equipped with a Dionex UVD3400 detector, a Dionex ASi-100 Autosampler (10 µL injection), a Dionex TCC-100 HPLC column thermostat (40° C.) and a DG1210 degasser. A gradient of 0-100% of acetonitrile in an aqueous phase (0.1% formic acid and 5% acetonitrile in demineralised water) was used as eluent.

Hydrogenolysis reaction: Samples were analysed on a Waters Symmetry Shield™ column (RP-8, 3.5 µM, 4.6×50 mM) using a Dionex P680 HPLC pump (0.8 mL·min-1) equipped with an ERC RefractoMax 520 detector, a Dionex ASi-100 Autosampler (10 µL injection) and a Dionex TCC-100 HPLC column thermostat (70° C.). 5 mM $H_2SO_4$ (pH 1.5) in demineralised water was used as eluent.

B) Preparation of the Carriers (MCC)

SRCC1 ($d_{50}$(vol)=4.4 µm, $d_{98}$(vol)=8.6 µm, SSA=39.9 $m^2g^{-1}$)

SRCC1 was obtained by preparing 10 litres of an aqueous suspension of ground calcium carbonate in a mixing vessel by adjusting the solids content of a ground marble calcium carbonate from Hustadmarmor Norway having a mass based particle size distribution of 90% less than 2 µm, as determined by sedimentation, such that a solids content of 15 wt.-%, based on the total weight of the aqueous suspension, is obtained. In addition, a solution was prepared containing 30 wt.-% phosphoric acid. Whilst mixing the slurry, 0.83 kg of the phosphoric acid solution was added to said suspension over a period of 10 min at a temperature of 70° C. Finally, after the addition of the phosphoric acid, the slurry was stirred for additional 5 min, before removing it from the vessel, filtering and drying.

SRCC2 ($d_{50}$(vol)=8.3 µm $d_{98}$(vol)=19.5 µm, SSA=74.4 $m^2g^{-1}$)

SRCC2 was obtained by preparing 10 litres of an aqueous suspension of ground calcium carbonate in a mixing vessel by adjusting the solids content of a ground marble calcium carbonate from Hustadmarmor Norway having a mass based particle size distribution of 90% less than 2 µm, as determined by sedimentation, such that a solids content of 15 wt.-%, based on the total weight of the aqueous suspension, is obtained. In addition, a solution was prepared by blending diluted phosphoric acid and aluminium sulphate hexadecahydrate, wherein the phosphoric acid had a concentration of 30 wt.-% and the aluminium sulphate hexadecahydrate was dosed with a mass 5% that of the neat phosphoric acid. Whilst mixing the slurry, 1.7 kg of the phosphoric acid/aluminium sulphate solution was added to said suspension over a period of 10 min at a temperature of 70° C. Finally, after the addition of the phosphoric acid, the slurry was stirred for additional 5 min, before removing it from the vessel, filtering and drying.

SRCC3 ($d_{50}$(vol)=8.2 µm, $d_{98}$(vol)=16.7 µm, SSA=90.0 $m^2g^{-1}$)

SRCC3 was obtained by preparing 10 litres of an aqueous suspension of ground calcium carbonate in a mixing vessel by adjusting the solids content of a ground marble calcium carbonate from Hustadmarmor Norway having a mass based particle size distribution of 90% less than 2 µm, as determined by sedimentation, such that a solids content of 10 wt.-%, based on the total weight of the aqueous suspension, is obtained. In addition, a solution was prepared by blending diluted phosphoric acid and citric acid, wherein the phosphoric acid had a concentration of 29 wt.-% and the citric acid was dosed with a mass 10% that of the neat phosphoric acid. Whilst mixing the slurry, 1.65 kg of the phosphoric acid/citric acid solution was added to said suspension over a period of 10 min at a temperature of 70° C. Finally, after the addition of the phosphoric acid, the slurry was stirred for additional 5 min, before removing it from the vessel, filtering and drying.

SRCC4 ($d_{50}$(vol)=6.7 µm, $d_{98}$(vol)=12.9 µm, SSA=146.5 $m^2g^{-1}$)

SRCC4 was obtained by preparing 10 l of an aqueous suspension of ground calcium carbonate in a mixing vessel by adjusting the solids content of a ground marble calcium carbonate from Hustadmarmor Norway having a mass based particle size distribution of 90% less than 2 µm, as determined by sedimentation, such that a solids content of 10 wt.-%, based on the total weight of the aqueous suspension, is obtained. In addition, a solution was prepared containing 30 wt.-% phosphoric acid while another was prepared containing 5 wt.% citric acid. Whilst mixing the slurry, 1.60 kg of the phosphoric acid solution was added to said suspension over a period of 10 min at a temperature of 70° C. Additionally, starting 2 min after the start of phosphoric acid addition, 0.05 kg of the citric acid solution was also added to the slurry. Finally, after the addition of the phosphoric acid, the slurry was stirred for additional 5 min, before removing it from the vessel, filtering and drying.

SRCC5 ($d_{50}$(vol)=7.1 µm, $d_{98}$(vol)=13.5 µm, SSA=119.2 $m^2g^{-1}$)

SRCC5 was obtained by preparing 10 litres of an aqueous suspension of ground calcium carbonate in a mixing vessel by adjusting the solids content of a ground marble calcium carbonate from Hustadmarmor Norway having a mass based particle size distribution of 90% less than 2 µm, as determined by sedimentation, such that a solids content of 10 wt.-%, based on the total weight of the aqueous suspension, is obtained. In addition, a solution was prepared containing 30 wt.-% phosphoric acid while another was prepared containing 5 wt.% citric acid. Whilst mixing the slurry, 1.60 kg of the phosphoric acid solution was added to said suspension over a period of 10 min at a temperature of 70° C. Additionally, starting 3 min after the start of phosphoric acid addition, 0.05 kg of the citric acid solution was also added to the slurry. Finally, after the addition of the phosphoric acid, the slurry was stirred for additional 5 min, before removing it from the vessel, filtering and drying.

TABLE 1

Quantitative Rietveld analysis (XRD) of the carriers (data normalised to 100% crystalline material).

| Mineral | Formula | SRCC1 | SRCC2 | SRCC3 | SRCC4 | SRCC5 |
|---|---|---|---|---|---|---|
| Calcite | $CaCO_3$ | 74.5 | 50.6 | 17.7 | 14.7 | 16.9 |
| Hydroxylapatite | $Ca_5(OH)(PO_4)_3$ | 25.5 | 49.4 | 82.3 | 85.3 | 83.1 |
| Total | | 100 | 100 | 100 | 100 | 100 |

TABLE 2

Hg Porosimetry of the carriers.

| | SRCC1[a] | SRCC2[b] | SRCC3[c] | SRCC4[d] | SRCC5[e] |
|---|---|---|---|---|---|
| Total intra particle intruded specific pore volume [μm/cm$^3$g$^{-1}$] | 0.412 | 0.919 | 2.195 | 1.235 | 1.287 |

[a] For the pore diameter range of 0.004 to 0.18 μm
[b] For the pore diameter range of 0.004 to 0.32 μm
[c] For the pore diameter range of 0.004 to 0.9 μm
[d] For the pore diameter range of 0.004 to 0.51 μm
[e] For the pore diameter range of 0.004 to 0.51 μm

C) Preparation of the Catalysts

Method 1: Non-Aqueous Impregnation in Ethanol

A slurry of the carrier (0.5 g) is prepared in an organic solvent (20 ml) in which the metal salt is already dissolved. The slurry is then stirred (18 h) and filtered off, dried under vacuum at ambient temperature for 18 h. The procedure can be repeated one time to increase the catalyst loading.

Method 2: Non-Aqueous Impregnation in Toluene

A slurry of the carrier (2 g) is prepared in an organic solvent (25 ml) in which the metal salt is also dissolved. The solvent is then evaporated under constant agitation to impregnate the catalyst onto the carrier and to obtain a homogenous powder. The material is then dried under vacuum at ambient temperature for 18 h and calcinated at 300° C.

Method 3: Aqueous Impregnation

A water soluble salt of the metal is first dissolved in water (4 ml) and the pH is adjusted to 5.5 to 6 by using $NaHCO_3$ (sat.). The solution is added to a slurry of the carrier (1.8-2.0 g) in water (8-12 ml). The mixture is heated to 70° C. for 30-90 min and then cooled to room temperature. The catalyst is filtered off, rinsed with water (3×4 ml), dried under vacuum at ambient temperature for 18 h and then calcinated at 300° C. for 3 h. The procedure can be repeated several times to increase the catalyst loading.

TABLE 3

Prepared catalysts (C1-C20)

| Ex. No. | Support used | Metal salt | Method No. | Solvent type | Catalyst amount[a] | Number of impregnations |
|---|---|---|---|---|---|---|
| C1 | SRCC1 | $Pd(acac)_2$ | 2 | Toluene | 5 | 1 |
| C2 | SRCC2 | $Pd(acac)_2$ | 2 | Toluene | 5 | 1 |
| C3 | SRCC3 | $Pd(acac)_2$ | 2 | Toluene | 5 | 1 |
| C4 | SRCC4 | $Pd(acac)_2$ | 2 | Toluene | 5 | 1 |
| C5 | SRCC5 | $Pd(acac)_2$ | 2 | Toluene | 5 | 1 |
| C6 | SRCC1 | $Pt(acac)_2$ | 2 | Toluene | 5 | 1 |
| C7 | SRCC2 | $Pt(acac)_2$ | 2 | Toluene | 5 | 1 |
| C8 | SRCC3 | $Pt(acac)_2$ | 2 | Toluene | 5 | 1 |
| C9 | SRCC4 | $Pt(acac)_2$ | 2 | Toluene | 5 | 1 |
| C10 | SRCC5 | $Pt(acac)_2$ | 2 | Toluene | 5 | 1 |
| C11 | SRCC1 | $Na_2PdCl_4$ | 3 | Water | 5 | 1 (30 min) |
| C12 | SRCC2 | $Na_2PdCl_4$ | 3 | Water | 5 | 1 (30 min) |
| C13 | SRCC3 | $Na_2PdCl_4$ | 3 | Water | 5 | 1 (30 min) |
| C14 | SRCC4 | $Na_2PdCl_4$ | 3 | Water | 5 | 1 (30 min) |
| C15 | SRCC5 | $Na_2PdCl_4$ | 3 | Water | 5 | 1 (30 min) |
| C16 | SRCC1 | $Na_2PtCl_4$ | 3 | Water | 5 | 2 (15 + 75 min) |
| C17 | SRCC2 | $Na_2PtCl_4$ | 3 | Water | 5 | 2 (45 + 45 min) |
| C18 | SRCC3 | $Na_2PtCl_4$ | 3 | Water | 5 | 2 (60 + 30 min) |
| C19 | SRCC4 | $Na_2PtCl_4$ | 3 | Water | 5 | 2 (60 + 30 min) |
| C20 | SRCC5 | $Na_2PtCl_4$ | 3 | Water | 5 | 1 (90 min) |
| CE1 | Palladium, 5% on calcium carbonate, unreduced, dry | | | | | |
| CE2 | Platinum, 5% on calcium carbonate, unreduced, dry | | | | | |

[a] Catalyst amount used for impregnation (wt.-% Pd or Pt)

Evaluation of Catalyst Loading:

The filtrate solution from aqueous impregnation C19 (SRCC4) was left standing until all soluble metal salt had precipitated as black material (i.e. until complete decolouration of the solution). The precipitate was weighed and the catalyst loading was calculated back from this value to be 4.6 wt.-% of Pt. The calculation was done from metallic platinum.

D) Application Examples

Suzuki reaction (Examples A1-A10, Comparative Examples CA1-CA5)

The coupling reaction between iodobenzene and phenylboronic acid was performed according to *Letters in Organic Chemistry*, 4, 2007, 13-15 with various catalysts loadings and catalysts type. In a typical reaction, 0.45 g of phenylboronic acid (1.5 equivalent, 3.7 mmol) was weighed into a 100 ml round bottom flask. Potassium carbonate (2.9 equivalent, 7.3 mmol, 1.0 g) was added to the mixture together with 80 mL solvent (ethanol 40% in water). The flask was closed with a septum, agitation was started and the flask was purged with a nitrogen flow. Iodobenzene (0.50 g, 2.5 mmol) was then added followed by the pre-weighed catalyst (in a closed vial). The nitrogen purge was continued for 10 to 15 min. Aliquots (ca 0.5 ml) were taken out of the mixture at regular intervals, extracted with 1 ml of heptane and analysed by HPLC using a UV diode array detector (238 nm). The conversion rate is summed up in Table 4.

At the end of the reaction, heptane was added to the reaction mixture and agitated for ca 15 min before transferring the contents to a 250 ml separation funnel and phases were separated and the organic phase was dried over $Na_2SO_4$ for ca 12 h and filtered. The clear organic layer was concentrated to dryness in a tared round bottom flask, using a rotary evaporator. The round bottom flask was weighed to determine the yield of the reaction. The aqueous layers from the extractions containing the catalyst were isolated by vacuum filtration using a fritted glass filter (porosity 3). The filter cake was washed with deionised water, ethanol, and heptane. The filters containing the filter cakes were placed in a vacuum oven and dried at 20° C. under full vacuum for >24 h. After drying the dried catalyst was collected from the filters and weighed into screw-cap glass vials to determine the recovered catalyst amount.

TABLE 4 comparison at similar catalyst loadings with a commercial supported catalyst.

| Example No. | Catalyst No. | Catalyst (mole-% Pd) | % conversion after ca. 4 h[a] | % conversion after ca. 7 h[a] |
|---|---|---|---|---|
| CA1 | CE1 | 1 | 47 | 87 |
| A1 | C11 | 1 | 71 | 93 |
| A2 | C14 | 1 | 96 | >99 |
| CA2 | CE1 | 0.6 | 36 | 75 |
| A3 | C11 | 0.6 | 63 | 89 |
| A4 | C14 | 0.6 | 75 | 96 |
| CA3 | CE1 | 0.3 | 8 | 34 |
| A5 | C11 | 0.3 | 31 | 56 |
| A6 | C14 | 0.3 | 44 | 64 |

[a]Based on iodobenzene

The above Table 4 shows the improved efficiency of the catalysts prepared according to the invention over a commercial Pd/CaCO$_3$ catalyst. The catalysts preparation can be found in table 3.

TABLE 5 recyclability of the catalysts.

| | | Example No. | | | | | |
|---|---|---|---|---|---|---|---|
| | | CA4 | CA5 | A7 | A8 | A9 | A10 |
| | | Catalyst No. | | | | | |
| | | CE1 | CE1 | C11 | C11 | C14 | C14 |
| | Initial Catalyst amount (mole-% Pd) | 1 | 0.6 | 1 | 0.6 | 1 | 0.6 |
| | % Pd on catalyst | 4.96 | 4.96 | n.a. | n.a. | 5.43 | 5.43 |
| 1st catalytic cycle | % conversion after ca. 4 h | 47 | 36 | 71 | 63 | 96 | 75 |
| | Yield 1st cycle [%] | 95 | 95 | 95 | 98 | 98 | 98 |
| | % catalyst recovered | 44 | 30 | 53 | 56 | 95 | >100 |
| | % Pd on catalyst after recovery | n.a. | n.a. | 4.94 | 4.75 | # | 3.28 |
| 2nd catalytic cycle | Yield 2nd cycle [%] | 85[a] | | 91[a] | | 93 | # |
| | % catalyst recovered | 15[a] | | 48[a] | | 82 | # |
| | % Pd on catalyst after recovery | 2.0[a] | | 4.0[a] | | 4.46 | # |
| 3rd catalytic cycle | Yield 3rd cycle [%] | # | # | # | # | 85 | # |
| | % catalyst recovered | # | # | # | # | 73 | # |
| | % Pd on catalyst after recovery | # | # | # | # | 3.7 | # |

[a]The recovered catalyst from the 1st catalytic cycle (trials with 1% and 0.6% catalyst) were combined and used for the 2nd catalytic cycle.
The experiments were not conducted.

The above Table 5 shows the good efficiency of the recovered catalysts, and that they are easier to recover than the commercial catalyst from the commercial sample.

Hydrogenolysis of Glycerol (Examples A11-A21)

The reactions were performed according to Catalysis Communications, 13, 2011, 1-5. A mixture of the catalyst (5 mole-% active metal, relative to glycerol) and 20 ml glycerol in water (100 mM) was put under 40 bar hydrogen pressure and then heated to 200° C. for 18 hours while stirring at 800 rpm. After cooling to room temperature a sample was taken for analysis. The sample was filtered and mixed with an equal amount of 5 mM H$_2$SO$_4$. The catalyst was filtered off, rinsed with water (3×1 ml) and dried under vacuum. The reaction mixtures were analysed by HPLC to determine the amounts of starting material (glycerol) to and the 4 major reaction products; lactic acid (LA), 1,2-propanediol (12-PD), ethylene glycol (EG) and ethanol (EtOH). In all cases these compounds made up ≥95% of the total peak area. Results are summarised in Table 6.

TABLE 6

Examples A11-20 and CA6 (hydrogenolysis of glycerol)

| Example No. | Catalyst No. | Impregnation method | Glycerol [%][a] | 12-PD [%][a] | EtOH [%][a] | EG [%][a] | LA [%][a] |
|---|---|---|---|---|---|---|---|
| CA6 | CE2 | — | 76 | 15 | 6.5 | 1.9 | 1.5 |
| A11 | C6 | Non-aqueous | 28 | 55 | 5.7 | 11 | 1.0 |
| A12 | C7 | Non-aqueous | 31 | 19 | 47 | 2.9 | 0.5 |
| A13 | C8 | Non-aqueous | 39 | 28 | 26 | 6.5 | 0.4 |
| A14 | C9 | Non-aqueous | 30 | 26 | 38 | 5.1 | 0.4 |
| A15 | C10 | Non-aqueous | 28 | 51 | 11 | 7.8 | 1.6 |
| A16 | C16 | Aqueous | 47 | 34 | 9.6 | 8.4 | 0.9 |
| A17 | C17 | Aqueous | 37 | 49 | 7.0 | 6.5 | 1.0 |
| A18 | C18 | Aqueous | 46 | 36 | 11 | 6.8 | 0.6 |
| A19 | C19 | Aqueous | 45 | 43 | 5.9 | 5.4 | 0.9 |
| A20 | C20 | Aqueous | 31 | 35 | 27 | 6.5 | 0.7 |

[a]Determined by HPLC analysis after reaction (peak area in % of total peaks area)

Table 6 shows that all catalysts according to the invention showed greater activity than the commercial catalyst used as comparative example.

The invention claimed is:

1. A catalyst system comprising a transition metal compound on a solid carrier, wherein the solid carrier is a surface-reacted calcium carbonate comprising ground natural calcium carbonate (GNCC) or precipitated calcium carbonate (PCC), and at least one water-insoluble calcium salt other than calcium carbonate, and wherein the surface-reacted calcium carbonate shows:

(i) a specific surface area of from 15 to 200 m²/g measured using nitrogen and the BET method according to ISO 9277:2010;
(ii) an intra-particle intruded specific pore volume in the range of from 0.1 to 2.3 cm³/g calculated from mercury porosimetry measurement; and
(iii) a ratio of the at least one water-insoluble calcium salt to calcium carbonate in the range of from 1:99 to 99:1 by weight, wherein the calcium carbonate comprises calcite, aragonite, and/or vaterite.

2. The catalyst system according to claim 1, wherein the at least one water-insoluble calcium salt is selected from the group consisting of octacalcium phosphate, hydroxylapatite, chlorapatite, fluorapatite, carbonate apatite and mixtures thereof.

3. The catalyst system according to claim 1, wherein the ratio of the at least one water-insoluble calcium salt to the calcium carbonate is in the range of from 1:9 to 9:1 by weight.

4. The catalyst system according to claim 1, wherein the transition metal compound is selected from the group consisting of palladium compounds, platinum compounds, copper compounds and mixtures thereof.

5. The catalyst system according to claim 1, wherein the transition metal compound is selected from the group consisting of elemental palladium, $Pd(acac)_2$, $Na_2PdCl_4$, $Pd(OAc)_2$, $Pd(PPh_3)_4$, $PdCl_2(PPh_3)_2$, $(dppf)PdCl_2$, $(dppe)PdCl_2$, $(dppp)PdCl_2$, $(dppb)PdCl_2$, $PdCl_2$, $(C_3H_5PdCl)_2$, bis(acetate)triphenyl-phosphine-palladium(II), $Pd(dba)_2$, $Pd(H_2NCH_2CH_2NH_2)Cl_2$, elemental platinum, $Na_2PtCl_6Pt(acac)_2$, $Na_2PtCl_4$, $H_2PtCl_6$, $(NH_4)_2[PtCl_6]$, $PtO_2H_2O$, $PtCl_4$, elemental copper, $Cu_2O$, $Cu_2S$, copper(I)-thiophene-2-carboxylate, CuBr, CuCN, CuCl, CuF, CuI, CuH, CuSCN, $CuBr_2$, $CuCO_3$, $CuCl_2$, $CuF_2$, $Cu(NO_3)_2$, $Cu_3(PO_4)_2$, CuO, $CuO_2$, $Cu(OH)_2$, $CuI_2$, CuS, $CuSO_4$, $Cu_2(OAc)_4$ and mixtures thereof.

6. The catalyst system according to claim 1, wherein the surface-reacted calcium carbonate has:
(i) a specific surface area in the range of from 27 to 180 m²/g, measured using nitrogen and the BET method according to ISO 9277:2010;
(ii) a $d_{50}$(vol) in the range of from 1 to 75 μm;
(iii) a $d_{98}$(vol) in the range of from 2 to 150 μm; and/or
(iv) an intra-particle intruded specific pore volume in the range of from 0.2 to 2.0 cm³/g calculated from mercury porosimetry measurement.

7. The catalyst system according to claim 1, wherein the catalyst system further comprises one or more reaction products obtained by reaction of the transition metal compound and the surface-reacted calcium carbonate.

8. The catalyst system according to claim 1, wherein the content of the transition metal compound and/or the one or more reaction products thereof is in the range of from 0.1 to 60 wt.-%, based on the weight of the transition metal compound per total weight of the catalyst system.

9. A carrier for transition metal-based catalysts comprising a catalyst system according to claim 1.

10. Granules, mouldings or extrudates comprising the catalyst system according to claim 1.

11. A method for manufacturing a catalyst system comprising a transition metal compound on a solid carrier, the method comprising:
(a) providing at least one surface-reacted calcium carbonate comprising ground natural calcium carbonate (GNCC) or precipitated calcium carbonate (PCC), and at least one water-insoluble calcium salt other than calcium carbonate;
(b) providing at least one transition metal compound; and
(c) contacting in a liquid medium, the surface-reacted calcium carbonate provided in step (a) and the transition metal compound provided in step (b) to obtain a mixture comprising surface-reacted calcium carbonate and a transition metal compound;
wherein the surface-reacted calcium carbonate shows:
(i) a specific surface area of from 15 to 200 m²/g measured using nitrogen and the BET method according to ISO 9277:2010;
(ii) an intra-particle intruded specific pore volume in the range of from 0.1 to 2.3 cm₃/g calculated from mercury porosimetry measurement; and
(iii) a ratio of the at least one water-insoluble calcium salt to calcium carbonate in the range of from 1:99 to 99:1 by weight. wherein the calcium carbonate comprises calcite, aragonite, and/or vaterite.

12. The method according to claim 11, wherein
(i) the at least one surface-reacted calcium carbonate of step (a) is provided in a liquid medium in form of a suspension; and/or
(ii) the at least one transition metal compound of step (b) is provided in a liquid medium in form of a solution or a suspension.

13. The method according to claim 11, wherein the method further comprises step (d) of removing at least part of the liquid medium contained in the mixture of step (c) by evaporation or filtration to obtain a concentrated mixture.

14. The method according to claim 11, wherein the method further comprises step (e) of thermally treating the mixture of step (c) or the concentrated mixture of step (d) at a temperature of below 400° C.

15. The method according to claim 11, wherein the transition metal compound is selected from the group consisting of palladium compounds, platinum compounds, copper compounds and mixtures thereof.

16. The method according to claim 11 wherein the transition metal compound is selected from the group consisting of elemental palladium, $Pd(acac)_2$, $Na2PdCl_4$, $Pd(OAc)_2$, $Pd(PPh_3)_4$, $PdCl_2(PPh_3)_2$, $(dppf)PdCl_2$, $(dppe)PdCl_2$, $(dppp)PdCl_2$, $(dppb)PdCl_2$, $PdCl_2$, $(C_3H_5PdCl)_2$, bis(acetate)triphenylphosphine-palladium(II), $Pd(dba)_2$, $Pd(H_2NCH_2CH_2NH_2)Cl_2$, elemental platinum, $Na_2PtCl_6Pt(acac)_2$, $Na_2PtCl_4$, $H_2PtCl_6$, $(NH_4)_2[PtCl_6]$, $PtO_2H_2O$, $PtCl_4$, elemental copper, $Cu_2O$, $Cu_2S$, copper(I)-thiophene-2-carboxylate, CuBr, CuCN, CuCl, CuF, CuI, CuH, CuSCN, $CuBr_2$, $CuCO_3$, $CuCl_2$, $CuF_2$, $Cu(NO_3)_2$, $Cu_3(PO_4)_2$, CuO, $CuO_2$, $Cu(OH)_2$, $CuI_2$, CuS, $CuSO_4$, $Cu_2(OAc)_4$ and mixtures thereof.

17. The method according to claim 11 wherein the liquid medium is a non-polar solvent, a polar solvent or a mixture thereof.

18. The method according to claim 11, wherein the transition metal compound is $Na_2PdCl_4$ and/or $Na_2PtCl_4$ and the liquid medium is a polar solvent.

19. A catalyst system obtained according to the method of claim 11.

20. A method of using a catalyst system comprising a transition metal compound on a solid carrier, wherein the solid carrier is a surface-reacted calcium carbonate comprising ground natural calcium carbonate (GNCC) or precipitated calcium carbonate (PCC), and at least one water-insoluble calcium salt other than calcium carbonate and wherein the surface-reacted calcium carbonate shows:
(i) a specific surface area of from 15 to 200 m²/g measured using nitrogen and the BET method according to ISO 9277:2010;

(ii) an intra-particle intruded specific pore volume in the range of from 0.1 to 2.3 cm$^3$/g calculated from mercury porosimetry measurement; and (iii) a ratio of the at least one water-insoluble calcium salt to calcium carbonate in the range of from 1:99 to 99:1 by weight, wherein the calcium carbonate comprises calcite, aragonite, and/or vaterite, in a process comprising:

(a) providing one or more reactants;

(b) providing said catalyst system; and (c) subjecting the one or more reactants provided in step (a) to a chemical reaction in the presence of the catalyst system provided in step (b).

21. The method according to claim 20, wherein the process further comprises step (d) of recovering the catalyst system following the chemical reaction of step (c) and recycling the transition metal.

22. The method according to claim 20, wherein the chemical reaction in step (c) is selected from one or more of the following reaction types: hydrogenolyses, C—C couplings and C—C cross couplings, C—N cross couplings, C—O cross couplings, C—S cross couplings, cycloaddition reactions, alkene hydrogenations and alkyne hydrogenations, allylic substitutions, reductions of nitro groups and hydrocarbonylations of aryl halides.

* * * * *